(12) United States Patent
Currie et al.

(10) Patent No.: US 8,735,360 B2
(45) Date of Patent: May 27, 2014

(54) TREATMENTS FOR GASTROINTESTINAL DISORDERS

(75) Inventors: Mark G. Currie, Sterling, MA (US); Daniel P. Zimmer, Somerville, MA (US); Angelika Fretzen, Somerville, MA (US); Marco Kessler, Danvers, MA (US); Brian Cali, Arlington, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/514,158

(22) PCT Filed: Dec. 7, 2010

(86) PCT No.: PCT/US2010/059294
§ 371 (c)(1),
(2), (4) Date: Jan. 18, 2013

(87) PCT Pub. No.: WO2011/071927
PCT Pub. Date: Jun. 16, 2011

(65) Prior Publication Data
US 2013/0130995 A1    May 23, 2013

Related U.S. Application Data

(60) Provisional application No. 61/267,316, filed on Dec. 7, 2009.

(51) Int. Cl.
| A61K 38/10 | (2006.01) |
| A61K 38/16 | (2006.01) |
| A61K 38/00 | (2006.01) |
| A61K 38/04 | (2006.01) |
| C07K 5/00  | (2006.01) |
| C07K 7/00  | (2006.01) |
| C07K 16/00 | (2006.01) |
| C07K 17/00 | (2006.01) |

(52) U.S. Cl.
USPC ......................... 514/21.4; 530/326

(58) Field of Classification Search
None
See application file for complete search history.

(56) References Cited

U.S. PATENT DOCUMENTS

| 5,518,888 A | 5/1996 | Waldman |
| 5,601,990 A | 2/1997 | Waldman |
| 5,879,656 A | 3/1999 | Waldman |
| 5,962,220 A | 10/1999 | Waldman |
| 6,060,037 A | 5/2000 | Waldman |
| 7,304,036 B2 * | 12/2007 | Currie et al. ............. 514/12.2 |
| 7,371,727 B2 | 5/2008 | Currie et al. |
| 7,704,947 B2 | 4/2010 | Currie et al. |
| 7,745,409 B2 | 6/2010 | Currie et al. |
| 7,772,188 B2 | 8/2010 | Currie et al. |
| 7,910,546 B2 | 3/2011 | Currie et al. |
| 8,080,526 B2 | 12/2011 | Currie et al. |
| 8,110,553 B2 | 2/2012 | Currie et al. |
| 8,507,447 B2 * | 8/2013 | Currie et al. ............. 514/21.5 |
| 2006/0281682 A1 * | 12/2006 | Currie et al. ............. 514/13 |
| 2009/0062207 A1 * | 3/2009 | Currie et al. ............. 514/14 |
| 2009/0253634 A1 | 10/2009 | Currie et al. |
| 2010/0048489 A1 | 2/2010 | Fretzen et al. |
| 2012/0039949 A1 | 2/2012 | Fretzen et al. |
| 2013/0085107 A1 * | 4/2013 | Currie et al. ............. 514/13.2 |
| 2013/0130995 A1 | 5/2013 | Currie et al. |

FOREIGN PATENT DOCUMENTS

| WO | 9939748 | 8/1999 |
| WO | 0180871 | 11/2001 |
| WO | 02070018 | 9/2002 |
| WO | 2005087797 | 9/2005 |
| WO | 2006138571 | 12/2006 |
| WO | 2007022531 | 2/2007 |
| WO | 2008151257 | 12/2008 |
| WO | 2011071927 | 10/2011 |
| WO | 2011156453 | 12/2011 |

OTHER PUBLICATIONS

Giblin et al. "Radiolabeled *Escherichia coli* heat-stable enterotoxin analogs for in vivo imaging of colorectal cancer", Nuclear Instruments & Methods in Physics Research, Section—B, vol. 241, No. 1-4, Dec. 1, 2005, pp. 689-692.

* cited by examiner

*Primary Examiner* — Cecilia J Tsang
*Assistant Examiner* — Zachary J Miknis
(74) *Attorney, Agent, or Firm* — Honigman Miller Schwartz & Cohn LLP; Kelly T. Murphy; Jonathan P. O'Brien

(57) ABSTRACT

Described herein are peptides, compositions, and related methods for treating upper gastrointestinal disorders and conditions (e.g., dyspepsia, gastroparesis, post-operative gastric ileus, a functional esophageal disorder, a functional gastroduodenal disorder, gastroesophageal reflux disease (GERD), or a duodenal or stomach ulcer) as well as other conditions and disorders that are described herein.

36 Claims, 1 Drawing Sheet

Dose response of Peptide 1 and Peptide 17 in a T84 cGMP assay at pH 5 and pH 8.
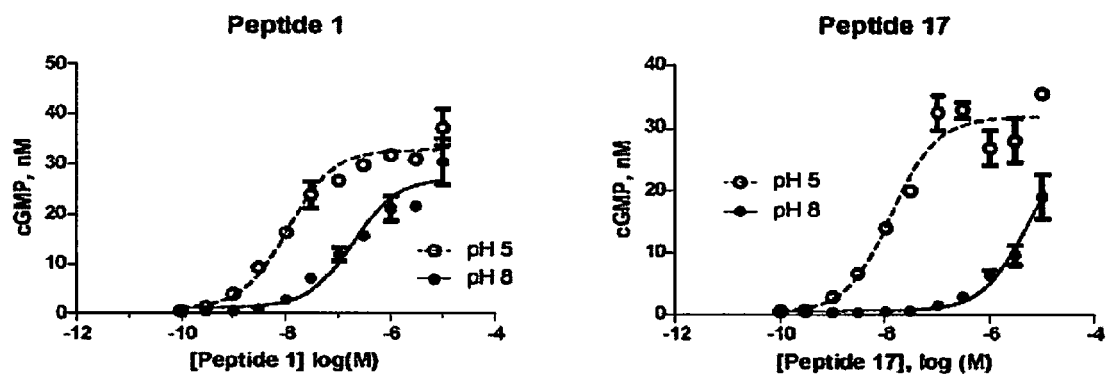

SEQUENCE LISTING

```
<160> NUMBER OF SEQ ID NOS: 71

<210> SEQ ID NO 1
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is Asn, D-Asn, Gln, D-Gln, Pro, D-Pro,
      Ala, beta-Ala, D-Ala, Val, D-Val, Gly, Thr, D-Thr, Asp, D-Asp,
      beta-carboxylated Asp, Glu, D-Glu, gamma-carboxylated Glu, alpha-
      aminosuberic acid (Asu), alpha-aminoadipic acid (Aad), or alpha-
      aminopimelic acid
<220> FEATURE:
<221> NAME/KEY: VARIANT
<222> LOCATION: (1)..(1)
<223> OTHER INFORMATION: Xaa1 may be modified on its amino group by
      methyl, ethanedioic acid, propanedioic acid, butanedioic acid,
      pentanedioic acid, hexanedioic acid, heptanedioic acid or
      octanedioic acid
<220> FEATURE:
<221> NAME/KEY: VARIANT
<222> LOCATION: (1)..(1)
```

-continued

<223> OTHER INFORMATION: if both Xaa2 and Xaa3 are absent, then Xaa1
      must be beta-carboxylated Asp or gamma-carboxylated Glu, or Xaa1
      must be Asp, D-Asp, Glu, D-Glu, Asu, Aad, or Apm and must be
      modified on its amino group by...<ctd below>
<220> FEATURE:
<221> NAME/KEY: VARIANT
<222> LOCATION: (1)..(1)
<223> OTHER INFORMATION: <ctd from above>...ethanedioic acid,
      propanedioic acid, butanedioic acid, pentanedioic acid,
      hexanedioic acid, heptanedioic acid, or octanedioic acid.
<220> FEATURE:
<221> NAME/KEY: MISC_FEATURE
<222> LOCATION: (2)..(3)
<223> OTHER INFORMATION: Xaa2 and Xaa 3 are independently Asp, beta-
      carboxylated Asp, Glu, gamma-carboxylated Glu, Asu, Aad, Apm, or
      are absent
<220> FEATURE:
<221> NAME/KEY: MISC_FEATURE
<222> LOCATION: (4)..(4)
<223> OTHER INFORMATION: Xaa4 is Cys or D-Cys
<220> FEATURE:
<221> NAME/KEY: MISC_FEATURE
<222> LOCATION: (6)..(6)
<223> OTHER INFORMATION: Xaa6 is Asp or Glu
<220> FEATURE:
<221> NAME/KEY: MISC_FEATURE
<222> LOCATION: (7)..(7)
<223> OTHER INFORMATION: Xaa7 is Tyr, Leu, Phe or Ile
<220> FEATURE:
<221> NAME/KEY: MISC_FEATURE
<222> LOCATION: (8)..(8)
<223> OTHER INFORMATION: Xaa8 is Cys or D-Cys
<220> FEATURE:
<221> NAME/KEY: MISC_FEATURE
<222> LOCATION: (14)..(14)
<223> OTHER INFORMATION: Xaa14 is Thr, Ala or Phe
<220> FEATURE:
<221> NAME/KEY: MISC_FEATURE
<222> LOCATION: (16)..(16)
<223> OTHER INFORMATION: Xaa16 is Cys or D-Cys
<220> FEATURE:
<221> NAME/KEY: MISC_FEATURE
<222> LOCATION: (17)..(17)
<223> OTHER INFORMATION: Xaa17 is Tyr, D-Tyr, or is absent

<400> SEQUENCE: 1

Xaa Xaa Xaa Xaa Cys Xaa Xaa Xaa Cys Asn Pro Ala Cys Xaa Gly Xaa
1               5                   10                  15

Xaa

<210> SEQ ID NO 2
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is Asn, D-Asn, Gln, D-Gln, Pro, D-Pro,
      Ala, beta-Ala, D-Ala, Val, D-Val, Gly, Thr, D-Thr, Asp, D-Asp, Glu
      or D-Glu
<220> FEATURE:
<221> NAME/KEY: MISC_FEATURE
<222> LOCATION: (2)..(2)
<223> OTHER INFORMATION: Xaa2 is Asp or Glu
<220> FEATURE:
<221> NAME/KEY: MISC_FEATURE
<222> LOCATION: (3)..(3)
<223> OTHER INFORMATION: Xaa3 is Asp or Glu, or is absent
<220> FEATURE:
<221> NAME/KEY: MISC_FEATURE
<222> LOCATION: (7)..(7)
<223> OTHER INFORMATION: Xaa7 is Tyr or Leu
<220> FEATURE:
<221> NAME/KEY: MISC_FEATURE
<222> LOCATION: (17)..(17)

<223> OTHER INFORMATION: Xaa17 is Tyr or is absent

<400> SEQUENCE: 2

Xaa Xaa Xaa Cys Cys Glu Xaa Cys Cys Asn Pro Ala Cys Thr Gly Cys
1               5                   10                  15

Xaa

<210> SEQ ID NO 3
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (15)..(15)
<223> OTHER INFORMATION: L-amino acid residue or D-amino acid residue

<400> SEQUENCE: 3

Asp Asp Cys Cys Glu Leu Cys Cys Asn Pro Ala Cys Thr Gly Cys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (15)..(15)
<223> OTHER INFORMATION: L-amino acid residue or D-amino acid residue

<400> SEQUENCE: 4

Asp Asp Cys Cys Glu Tyr Cys Cys Asn Pro Ala Cys Thr Gly Cys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 5

Asp Asp Cys Cys Glu Leu Cys Cys Asn Pro Ala Cys Thr Gly Cys Tyr
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetically generated peptide
<220> FEATURE:

```
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 6

Asp Asp Cys Cys Glu Tyr Cys Cys Asn Pro Ala Cys Thr Gly Cys Tyr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 7

Asn Asp Asp Cys Cys Glu Leu Cys Cys Asn Pro Ala Cys Thr Gly Cys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 8

Asn Asp Asp Cys Cys Glu Tyr Cys Cys Asn Pro Ala Cys Thr Gly Cys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (17)..(17)
<223> OTHER INFORMATION: L-amino acid residue or D-amino acid residue

<400> SEQUENCE: 9

Asn Asp Asp Cys Cys Glu Leu Cys Cys Asn Pro Ala Cys Thr Gly Cys
1               5                   10                  15

Tyr

<210> SEQ ID NO 10
```

```
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (17)..(17)
<223> OTHER INFORMATION: L-amino acid residue or D-amino acid residue

<400> SEQUENCE: 10

Asn Asp Asp Cys Cys Glu Tyr Cys Cys Asn Pro Ala Cys Thr Gly Cys
1               5                   10                  15

Tyr

<210> SEQ ID NO 11
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 11

Ala Asp Asp Cys Cys Glu Leu Cys Cys Asn Pro Ala Cys Thr Gly Cys
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or D-amino acid residue
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 12

Ala Asp Asp Cys Cys Glu Tyr Cys Cys Asn Pro Ala Cys Thr Gly Cys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: bAla
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 13
```

Ala Asp Asp Cys Cys Glu Leu Cys Cys Asn Pro Ala Cys Thr Gly Cys
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: bAla
<220> FEATURE:
<221> NAME/KEY: MISC_FEATURE
<222> LOCATION: (16)..(16)
<223> OTHER INFORMATION: L-amino acid residue or D-amino acid residue

<400> SEQUENCE: 14

Ala Asp Asp Cys Cys Glu Tyr Cys Cys Asn Pro Ala Cys Thr Gly Cys
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 15

Ala Asp Asp Cys Cys Glu Leu Cys Cys Asn Pro Ala Cys Thr Gly Cys
1               5                   10                  15
Tyr

<210> SEQ ID NO 16
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 16

Ala Asp Asp Cys Cys Glu Tyr Cys Cys Asn Pro Ala Cys Thr Gly Cys
1               5                   10                  15
Tyr

<210> SEQ ID NO 17
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES

```
<222> LOCATION: (1)..(1)
<223> OTHER INFORMATION: bAla
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 17

Ala Asp Asp Cys Cys Glu Leu Cys Cys Asn Pro Ala Cys Thr Gly Cys
1               5                   10                  15
Tyr

<210> SEQ ID NO 18
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: bAla
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 18

Ala Asp Asp Cys Cys Glu Tyr Cys Cys Asn Pro Ala Cys Thr Gly Cys
1               5                   10                  15
Tyr

<210> SEQ ID NO 19
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 19

Pro Asp Asp Cys Cys Glu Leu Cys Cys Asn Pro Ala Cys Thr Gly Cys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 20

Pro Asp Asp Cys Cys Glu Tyr Cys Cys Asn Pro Ala Cys Thr Gly Cys
1               5                   10                  15
```

-continued

```
<210> SEQ ID NO 21
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 21

Pro Asp Asp Cys Cys Glu Leu Cys Cys Asn Pro Ala Cys Thr Gly Cys
1               5                   10                  15

Tyr

<210> SEQ ID NO 22
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 22

Pro Asp Asp Cys Cys Glu Tyr Cys Cys Asn Pro Ala Cys Thr Gly Cys
1               5                   10                  15

Tyr

<210> SEQ ID NO 23
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 23

Thr Asp Asp Cys Cys Glu Leu Cys Cys Asn Pro Ala Cys Thr Gly Cys
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
```

<223> OTHER INFORMATION: L-amino acid residue or a D-amino acid residue

<400> SEQUENCE: 24

Thr Asp Asp Cys Cys Glu Tyr Cys Cys Asn Pro Ala Cys Thr Gly Cys
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 25

Thr Asp Asp Cys Cys Glu Leu Cys Cys Asn Pro Ala Cys Thr Gly Cys
1               5                   10                  15

Tyr

<210> SEQ ID NO 26
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 26

Thr Asp Asp Cys Cys Glu Tyr Cys Cys Asn Pro Ala Cys Thr Gly Cys
1               5                   10                  15

Tyr

<210> SEQ ID NO 27
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 27

Gly Asp Asp Cys Cys Glu Leu Cys Cys Asn Pro Ala Cys Thr Gly Cys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)

<223> OTHER INFORMATION: L-amino acid residue or a D-amino acid residue

<400> SEQUENCE: 28

Gly Asp Asp Cys Cys Glu Tyr Cys Cys Asn Pro Ala Cys Thr Gly Cys
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 29

Gly Asp Asp Cys Cys Glu Leu Cys Cys Asn Pro Ala Cys Thr Gly Cys
1               5                   10                  15

Tyr

<210> SEQ ID NO 30
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 30

Gly Asp Asp Cys Cys Glu Tyr Cys Cys Asn Pro Ala Cys Thr Gly Cys
1               5                   10                  15

Tyr

<210> SEQ ID NO 31
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 31

Asp Asp Asp Cys Cys Glu Leu Cys Cys Asn Pro Ala Cys Thr Gly Cys
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)

<223> OTHER INFORMATION: L-amino acid residue or a D-amino acid residue

<400> SEQUENCE: 32

Asp Asp Asp Cys Cys Glu Tyr Cys Cys Asn Pro Ala Cys Thr Gly Cys
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 33

Asp Asp Asp Cys Cys Glu Leu Cys Cys Asn Pro Ala Cys Thr Gly Cys
1               5                   10                  15

Tyr

<210> SEQ ID NO 34
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 34

Asp Asp Asp Cys Cys Glu Tyr Cys Cys Asn Pro Ala Cys Thr Gly Cys
1               5                   10                  15

Tyr

<210> SEQ ID NO 35
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: L-amino acid residue or a D-amino acid residue

<400> SEQUENCE: 35

Glu Glu Cys Cys Glu Leu Cys Cys Asn Pro Ala Cys Thr Gly Cys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)

-continued

<223> OTHER INFORMATION: L-amino acid residue or a D-amino acid residue
<220> FEATURE:
<221> NAME/KEY: MISC_FEATURE
<222> LOCATION: (15)..(15)
<223> OTHER INFORMATION: L-amino acid residue or a D-amino acid residue

<400> SEQUENCE: 36

Glu Glu Cys Cys Glu Tyr Cys Cys Asn Pro Ala Cys Thr Gly Cys
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 37

Glu Glu Cys Cys Glu Leu Cys Cys Asn Pro Ala Cys Thr Gly Cys Tyr
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 38

Glu Glu Cys Cys Glu Tyr Cys Cys Asn Pro Ala Cys Thr Gly Cys Tyr
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 39

Glu Glu Glu Cys Cys Glu Leu Cys Cys Asn Pro Ala Cys Thr Gly Cys
1               5                   10                  15

<210> SEQ ID NO 40
<211> LENGTH: 16
<212> TYPE: PRT
<213> ORGANISM: Artificial Sequence
<220> FEATURE:

```
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 40

Glu Glu Glu Cys Cys Glu Tyr Cys Cys Asn Pro Ala Cys Thr Gly Cys
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 41

Glu Glu Glu Cys Cys Glu Leu Cys Cys Asn Pro Ala Cys Thr Gly Cys
1               5                   10                  15

Tyr

<210> SEQ ID NO 42
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (17)..(17)
<223> OTHER INFORMATION: L-amino acid residue or a D-amino acid residue

<400> SEQUENCE: 42

Glu Glu Glu Cys Cys Glu Tyr Cys Cys Asn Pro Ala Cys Thr Gly Cys
1               5                   10                  15

Tyr

<210> SEQ ID NO 43
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (15)..(15)
<223> OTHER INFORMATION: L-amino acid residue or a D-amino acid residue

<400> SEQUENCE: 43

Glu Asp Cys Cys Glu Leu Cys Cys Asn Pro Ala Cys Thr Gly Cys
1               5                   10                  15
```

```
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (15)..(15)
<223> OTHER INFORMATION: L-amino acid residue or a D-amino acid residue

<400> SEQUENCE: 44

```
Glu Asp Cys Cys Glu Tyr Cys Cys Asn Pro Ala Cys Thr Gly Cys
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 45

```
Glu Asp Cys Cys Glu Leu Cys Cys Asn Pro Ala Cys Thr Gly Cys Tyr
1               5                   10                  15
```

<210> SEQ ID NO 46
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: L-amino acid residue or a D-amino acid residue
<220> FEATURE:
<221> NAME/KEY: MISC_FEATURE
<222> LOCATION: (16)..(16)
<223> OTHER INFORMATION: L-amino acid residue or a D-amino acid residue

<400> SEQUENCE: 46

```
Glu Asp Cys Cys Glu Tyr Cys Cys Asn Pro Ala Cys Thr Gly Cys Tyr
1               5                   10                  15
```

<210> SEQ ID NO 47
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: D amino acid

<400> SEQUENCE: 47

```
Asp Asp Asp Cys Cys Glu Tyr Cys Cys Asn Pro Ala Cys Thr Gly Cys
```

<210> SEQ ID NO 48
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: D amino acid

<400> SEQUENCE: 48

```
Ala Asp Asp Cys Cys Glu Tyr Cys Cys Asn Pro Ala Cys Thr Gly Cys
1               5                   10                  15

Tyr
```

<210> SEQ ID NO 49
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: D amino acid

<400> SEQUENCE: 49

```
Asn Asp Asp Cys Cys Glu Leu Cys Cys Asn Pro Ala Cys Thr Gly Cys
1               5                   10                  15

Tyr
```

<210> SEQ ID NO 50
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: D amino acid

<400> SEQUENCE: 50

```
Ala Asp Asp Cys Cys Glu Leu Cys Cys Asn Pro Ala Cys Thr Gly Cys
1               5                   10                  15

Tyr
```

<210> SEQ ID NO 51
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: D amino acid

<400> SEQUENCE: 51

```
Asp Asp Asp Cys Cys Glu Leu Cys Cys Asn Pro Ala Cys Thr Gly Cys
1               5                   10                  15

Tyr
```

```
<210> SEQ ID NO 52
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: D amino acid

<400> SEQUENCE: 52

Asp Asp Asp Cys Cys Glu Leu Cys Cys Asn Pro Ala Cys Thr Gly Cys
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 53

Asn Asp Asp Cys Cys Glu Tyr Cys Cys Asn Pro Ala Cys Thr Gly Cys
1               5                   10                  15

Tyr

<210> SEQ ID NO 54
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 54

Asp Asp Cys Cys Glu Tyr Cys Cys Asn Pro Ala Cys Thr Gly Cys Tyr
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 55

Asp Asp Asp Cys Cys Glu Tyr Cys Cys Asn Pro Ala Cys Thr Gly Cys
1               5                   10                  15

Tyr

<210> SEQ ID NO 56
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 56

Gly Asp Asp Cys Cys Glu Tyr Cys Cys Asn Pro Ala Cys Thr Gly Cys
1               5                   10                  15

Tyr

<210> SEQ ID NO 57
<211> LENGTH: 17
<212> TYPE: PRT
<213> ORGANISM: Artificial Sequence
```

```
<220> FEATURE:
<223> OTHER INFORMATION: Synthetically generated peptide

<400> SEQUENCE: 57

Pro Asp Asp Cys Cys Glu Tyr Cys Cys Asn Pro Ala Cys Thr Gly Cys
1               5                   10                  15

Tyr

<210> SEQ ID NO 58
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 58

Ala Asp Asp Cys Cys Glu Tyr Cys Cys Asn Pro Ala Cys Thr Gly Cys
1               5                   10                  15

Tyr

<210> SEQ ID NO 59
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 59

Asn Asp Asp Cys Cys Glu Leu Cys Cys Asn Pro Ala Cys Thr Gly Cys
1               5                   10                  15

Tyr

<210> SEQ ID NO 60
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 60

Ala Asp Asp Cys Cys Glu Leu Cys Cys Asn Pro Ala Cys Thr Gly Cys
1               5                   10                  15

Tyr

<210> SEQ ID NO 61
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: bAla

<400> SEQUENCE: 61

Ala Asp Asp Cys Cys Glu Leu Cys Cys Asn Pro Ala Cys Thr Gly Cys
1               5                   10                  15

Tyr

<210> SEQ ID NO 62
<211> LENGTH: 16
<212> TYPE: PRT
<213> ORGANISM: Artificial Sequence
<220> FEATURE:
```

<223> OTHER INFORMATION: Synthetically generated peptide

<400> SEQUENCE: 62

Asp Asp Cys Cys Glu Leu Cys Cys Asn Pro Ala Cys Thr Gly Cys Tyr
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 63

Asp Asp Asp Cys Cys Glu Leu Cys Cys Asn Pro Ala Cys Thr Gly Cys
1               5                   10                  15

Tyr

<210> SEQ ID NO 64
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 64

Pro Asp Asp Cys Cys Glu Leu Cys Cys Asn Pro Ala Cys Thr Gly Cys
1               5                   10                  15

Tyr

<210> SEQ ID NO 65
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 65

Gly Asp Asp Cys Cys Glu Leu Cys Cys Asn Pro Ala Cys Thr Gly Cys
1               5                   10                  15

Tyr

<210> SEQ ID NO 66
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 66

Asp Asp Asp Cys Cys Glu Leu Cys Cys Asn Pro Ala Cys Thr Gly Cys
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 67

Glu Glu Glu Cys Cys Glu Tyr Cys Cys Asn Pro Ala Cys Thr Gly Cys
1               5                   10                  15

Tyr

```
<210> SEQ ID NO 68
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is Asn, D-Asn, Gln, D-Gln, Pro, D-Pro,
      Ala, beta-Ala, D-Ala, Val, D-Val, Gly, Thr, D-Thr, Asp, D-Asp,
      Glu, or D-Glu
<220> FEATURE:
<221> NAME/KEY: MISC_FEATURE
<222> LOCATION: (3)..(3)
<223> OTHER INFORMATION: Xaa3 is Asp or is absent
<220> FEATURE:
<221> NAME/KEY: MISC_FEATURE
<222> LOCATION: (7)..(7)
<223> OTHER INFORMATION: Xaa7 is Tyr or Leu
<220> FEATURE:
<221> NAME/KEY: MISC_FEATURE
<222> LOCATION: (17)..(17)
<223> OTHER INFORMATION: Xaa17 is Tyr or is absent

<400> SEQUENCE: 68

Xaa Asp Xaa Cys Cys Glu Xaa Cys Cys Asn Pro Ala Cys Thr Gly Cys
1               5                   10                  15

Xaa

<210> SEQ ID NO 69
<211> LENGTH: 14
<212> TYPE: PRT
<213> ORGANISM: Artificial sequence
<220> FEATURE:
<223> OTHER INFORMATION: Synthetically generated peptide

<400> SEQUENCE: 69

Cys Cys Glu Leu Cys Cys Asn Pro Ala Cys Thr Gly Cys Tyr
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 70

Cys Cys Glu Phe Cys Cys Asn Pro Ala Cys Thr Gly Cys Tyr
1               5                   10

<210> SEQ ID NO 71
<211> LENGTH: 18
<212> TYPE: PRT
<213> ORGANISM: Escherichia coli

<400> SEQUENCE: 71

Asn Thr Phe Tyr Cys Cys Glu Leu Cys Cys Asn Pro Ala Cys Ala Gly
1               5                   10                  15

Cys Tyr
```

TREATMENTS FOR GASTROINTESTINAL DISORDERS

PRIORITY CLAIM

This application is a national phase application of PCT/US2010/059294, filed on Dec. 7, 2010, which claims priority to U.S. Provisional Patent Application Ser. No. 61/267,316, filed Dec. 7, 2009. The entire contents of the aforementioned applications are incorporated herein by reference.

FIELD OF THE INVENTION

This invention relates to peptides, compositions and methods for treating upper gastrointestinal disorders.

SEQUENCE LISTING

This application incorporates by reference in its entirety the Sequence Listing entitled "IW076PCT1US1sequence_ST25.txt" (30.4 kilobytes) which was created Jan. 14, 2013 and filed electronically herewith.

BACKGROUND

Functional dyspepsia (FD) and gastroparesis (GP) are upper gastrointestinal (GI) disorders that are collectively characterized by symptoms that include bloating, epigastric (upper abdominal) pain and/or burning, nausea, vomiting and early satiation. Therapeutic options for FD and GP patients are extremely limited, due to both lack of efficacy and poor safety profiles for existing therapies.

Dyspepsia is defined as the presence of one or more dyspepsia symptoms (epigastric pain, burning, bothersome postprandial fullness, and early satiation) that are considered to originate from the gastroduodenal region, in the absence of any organic, systemic, or metabolic disease that is likely to explain the symptoms (see Drossman, D. A., ed., *Rome III: The Functional Gastrointestinal Disorders*, 3rd Ed., McLean, VA: Degnon Associates, Inc., 2006). FD refers to dyspepsia that has no structural explanation after standard medical investigations, including upper endoscopy. Pathophysiological mechanisms that may be involved in FD include, among others, delayed gastric emptying, impaired gastric accommodation, hypersensitivity to gastric distention, altered duodenal sensitivity to lipids or acid, and abnormal duodenojejunal motility. Prolonged duodenal acid exposure is also seen in some FD and GP patients, and this exposure may slow gastric emptying and cause FD or GP-like symptoms. Dyspepsia is a common syndrome that accounts for about 30% of cases seen by gastroenterologists, with FD representing about 60% of all such dyspepsia cases.

GP refers to abnormal gastric motility characterized by delayed gastric emptying in the absence of mechanical obstruction. GP may be idiopathic or may be caused by various conditions, including Type I or Type II diabetes mellitus, viral infection, scleroderma, nervous system disorders such as Parkinson's disease, metabolic disorders such as hypothyroidism, post-operative ileus, and certain medications, including narcotic pain medications, tricyclic antidepressants and calcium channel blockers. Treatment for cancer, including chemotherapeutic drugs and radiation to the chest and abdomen can also cause gastroparesis, either temporarily or permanently. The most common symptoms are nausea, vomiting, bloating, epigastric pain, weight loss and early satiation. Gastroparesis is a chronic condition that can lead to frequent hospitalization, decreased quality of life, and increased disability and, in severe cases, increased mortality. Severe, symptomatic GP is common in individuals suffering from diabetes, affecting from 5-10% of diabetics for a total patient population of 1 million in the U.S. alone.

Conventional treatment options for FD and GP, as well as other upper gastrointestinal disorders, have been of limited efficacy for many patients. Thus, there remains a need for new compounds and methods of treating FD, GP and other gastrointestinal disorders.

SUMMARY

The present invention features peptides, compositions, and related methods for treating upper gastrointestinal disorders and conditions (e.g., dyspepsia, gastroparesis (GP), post-operative gastric ileus, a functional esophageal disorder, a functional gastroduodenal disorder, gastroesophageal reflux disease (GERD), or a duodenal or stomach ulcer) as well as other conditions and disorders described herein. The compositions feature peptides that activate guanylate cyclase C (GC-C) in the upper GI but activate GC-C in the lower GI much more weakly or not at all. Without being bound by any particular theory, the peptides of the invention are useful because they may alleviate symptoms of upper GI disorders (in whole or in part by increasing upper GI motility and/or reducing epigastric pain/discomfort and bloating) without causing pronounced effects in the lower GI tract (e.g., dose-limiting alterations in bowel habits, including diarrhea) at dose levels and dosing frequency sufficient to reduce upper GI symptoms.

One aspect of the present inventions provides a peptide comprising the amino acid sequence:

$Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ (SEQ ID NO:1), or a pharmaceutically acceptable salt thereof; wherein $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, α-aminosuberic acid (Asu), α-aminoadipic acid (Aad), or α-aminopimelic acid (Apm);

$Xaa_2$ is Asp, β-carboxylated Asp, Glu, γ-carboxylated Glu, Asu, Aad, Apm, or is absent;

$Xaa_3$ is Asp, β-carboxylated Asp, Glu, γ-carboxylated Glu, Asu, Aad, Apm, or is absent;

$Xaa_4$ is Cys or D-Cys;

$Xaa_6$ is Asp or Glu;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

$Xaa_1$ may be modified on its amino group by methyl, ethanedioic acid, propanedioic acid, butanedioic acid, pentanedioic acid, hexanedioic acid, heptanedioic acid or octanedioic acid; and if both $Xaa_2$ and $Xaa_3$ are absent, then $Xaa_1$ must be β-carboxylated Asp or γ-carboxylated Glu, or $Xaa_1$ must be Asp, D-Asp, Glu, D-Glu, Asu, Aad, or Apm and must be modified on its amino group by ethanedioic acid, propanedioic acid, butanedioic acid, pentanedioic acid, hexanedioic acid, heptanedioic acid or octanedioic acid.

A second aspect of the present invention provides pharmaceutical compositions comprising a peptide of the present invention.

A third aspect of the present invention provides methods for treating a gastrointestinal disorder, which include administering a pharmaceutical composition according to the present invention.

The details of one or more embodiments of the invention are set forth in the accompanying description.

BRIEF DESCRIPTION OF THE FIGURE

FIG. 1 shows the dose response of exemplary peptides of the present invention including Peptide 1 and Peptide 17 in a T84 cell cGMP assay at pH 5 and pH 8.

The FIGURE is provided by way of example and is not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. In addition, cGMP, which is secreted bidirectionally from the epithelium into the mucosa and lumen, has also been shown to dampen afferent C fiber firing, suggesting a potential mechanism for the observed analgesic effects of GC-C agonists on visceral pain.

Linaclotide, a peptide GC-C agonist that is orally administered and currently in clinical trials for treatment of irritable bowel syndrome with constipation (IBS-c) and chronic constipation (CC), has numerous effects on lower GI physiology including: (1) reduced visceral pain, (2) reduced bloating, and (3) increased GI transit, which can lead to increased stool frequency and improved stool consistency. Orally administered linaclotide acts locally by activating GC-C at the luminal surface; there are no detectable levels of linaclotide seen systemically after oral administration at therapeutic dose levels. Thus, the results from clinical trials of linaclotide, as well as preclinical studies that have been done with linaclotide and related peptides, suggest that GC-C peptide agonists may be used therapeutically.

It would be useful to have a GC-C agonist that could be used to alleviate upper GI disorders and symptoms (e.g., functional dyspepsia (FD) and gastroparesis (GP)) without promoting pronounced effects on bowel habits that could result from stimulation of GC-C in lower parts of the GI tract. Such a GC-C agonist would decrease the potential for lower GI adverse events, including altered bowel habits and diarrhea. The GC-C peptide agonists described herein are more active in the upper GI tract (e.g., the stomach and duodenum), and less active in the lower GI tract. Such agonists would have benefits in patients who suffer from upper GI disorders (e.g., FD and GP) by (1) reducing visceral pain through cGMP production and or/other mechanisms, (2) decreasing bloating, (3) increasing gastric emptying and/or upper small intestine transit (e.g., duodenal transit), and (4) neutralizing acid in the duodenum by promoting bicarbonate secretion. Importantly, these agonists, by virtue of their targeted activity in the upper GI, would be able to alleviate the symptoms of FD and GP without causing pronounced effects on bowel habits (e.g., that can result from stimulation of GC-C in the lower small intestine).

In one aspect, the invention provides novel GC-C peptide agonists useful for the treatment of gastrointestinal disorders, particularly upper GI disorders such as FD and GP. The GC-C peptide agonists described herein have GC-C agonist activity that is pH-dependent. The pH of the GI tract varies along its length in normal, healthy individuals, being lowest in the stomach (pH 1.5-3.5), rising to approximately pH 6 in the upper duodenum and increasing further (pH 7-8) in lower parts of the small intestine. Large intestine pH tends to vary from pH 6 to pH 8. The GC-C agonist peptides described herein are more active at a lower pH and less active at a higher pH. Thus, the GC-C agonist peptides are more active in the upper GI, including the esophagus, stomach and upper small intestine (upper duodenum) but are less active as they traverse the rest of the small intestine. Exemplary GC-C agonist peptides described herein exhibit a 10- to 1000-fold decreased potency at pH 8 compared to their potency at pH 5 as determined by in vitro assays that measure ability to bind and/or stimulate GC-C. Some GC-C peptide agonists such as those exemplified in peptides 1 and 2, show little or no pH sensitivity with regard to binding and/or activation of GC-C. In general, the peptides described in the present invention demonstrate that addition of specific N-terminal amino acids render the GC-C peptide agonist activity more sensitive to changes in pH.

In several embodiments, the present invention provides a peptide or pharmaceutically acceptable salt thereof, wherein the peptide comprises the amino acid sequence:

$Xaa_1$ $Xaa_2$ $Xaa_3$ $Xaa_4Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ (SEQ ID NO: 1), or a pharmaceutically acceptable salt thereof; wherein $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, α-aminosuberic acid (Asu), α-aminoadipic acid (Aad), or α-aminopimelic acid (Apm);

$Xaa_2$ is Asp, β-carboxylated Asp, Glu, γ-carboxylated Glu, Asu, Aad, Apm, or is absent;

$Xaa_3$ is Asp, β-carboxylated Asp, Glu, γ-carboxylated Glu, Asu, Aad, Apm, or is absent;

$Xaa_4$ is Cys or D-Cys;

$Xaa_6$ is Asp or Glu;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

$Xaa_1$ may be modified on its amino group by methyl, ethanedioic acid, propanedioic acid, butanedioic acid, pentanedioic acid, hexanedioic acid, heptanedioic acid or octanedioic acid; and if both $Xaa_2$ and $Xaa_3$ are absent, then $Xaa_1$ must be β-carboxylated Asp or γ-carboxylated Glu, or $Xaa_1$ must be Asp, D-Asp, Glu, D-Glu, Asu, Aad, or Apm and must be modified on its amino group by ethanedioic acid, propanedioic acid, butanedioic acid, pentanedioic acid, hexanedioic acid, heptanedioic acid or octanedioic acid.

In several embodiments, $Xaa_1$ is modified on its amino group at either or both hydrogen atoms by methyl, ethanedioic acid, propanedioic acid, butanedioic acid, pentanedioic acid, hexanedioic acid, heptanedioic acid or octanedioic acid.

In several embodiments, $Xaa_1$ is not modified on its amino group when either or both of $Xaa_2$ and $Xaa_3$ are present.

In several embodiments, $Xaa_2$ is Asp or Glu. In others, $Xaa_2$ is Asp.

In several embodiments, $Xaa_2$ and $Xaa_3$ are both present. In several embodiments, $Xaa_2$ is present and $Xaa_3$ is absent. In several embodiments, $Xaa_2$ and $Xaa_3$ are both absent In several embodiments, $Xaa_3$ is Asp or Glu. In others, $Xaa_3$ is Asp.

In several embodiments, either or both of $Xaa_2$ and $Xaa_3$ are present and $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, Asu, Aad or Apm. In further embodiments, $Xaa_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu. In yet further embodiments, $Xaa_1$ is Asp, D-Asp, Glu or D-Glu.

In several embodiments, $Xaa_4$ is Cys.
In several embodiments, $Xaa_6$ is Glu.
In several embodiments, $Xaa_7$ is Tyr or Leu.
In several embodiments, $Xaa_8$ is Cys.
In several embodiments, $Xaa_{14}$ is Thr.
In several embodiments, $Xaa_{16}$ is Cys.
In several embodiments, $Xaa_{17}$ is Tyr.
In several embodiments, $Xaa_{17}$ is absent.

In some embodiments, the present invention provides a peptide or pharmaceutically acceptable salt thereof, wherein said peptide comprises the amino acid sequence $Xaa_1\ Xaa_2\ Xaa_3\ Cys_4\ Cys_5\ Glu_6\ Xaa_7\ Cys_8\ Cys_9\ Asn_{10}\ Pro_{11}\ Ala_{12}\ Cys_{13}\ Thr_{14}\ Gly_{15}\ Cys_{16}\ Xaa_{17}$ (SEQ ID NO:2); wherein $Xaa_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;

$Xaa_2$ is Asp or Glu;
$Xaa_3$ is Asp, Glu, or is absent;
$Xaa_7$ is Tyr or Leu; and
$Xaa_{17}$ is Tyr or is absent.

In some embodiments, the present invention provides a peptide or pharmaceutically acceptable salt thereof, wherein said peptide comprises:

```
                                                    (SEQ ID NO: 3)
Asp Asp Cys Cys Glu Leu Cys Cys Asn Pro Ala Cys Thr Gly Cys;

(SEQ ID NO: 4)
Asp Asp Cys Cys Glu Tyr Cys Cys Asn Pro Ala Cys Thr Gly Cys;

(SEQ ID NO: 5)
Asp Asp Cys Cys Glu Leu Cys Cys Asn Pro Ala Cys Thr Gly Cys Tyr;

(SEQ ID NO: 6)
Asp Asp Cys Cys Glu Tyr Cys Cys Asn Pro Ala Cys Thr Gly Cys Tyr;

(SEQ ID NO: 7)
Asn Asp Asp Cys Cys Glu Leu Cys Cys Asn Pro Ala Cys Thr Gly Cys;

(SEQ ID NO: 8)
Asn Asp Asp Cys Cys Glu Tyr Cys Cys Asn Pro Ala Cys Thr Gly Cys;

(SEQ ID NO: 9)
Asn Asp Asp Cys Cys Glu Leu Cys Cys Asn Pro Ala Cys Thr Gly Cys Tyr;

(SEQ ID NO: 10)
Asn Asp Asp Cys Cys Glu Tyr Cys Cys Asn Pro Ala Cys Thr Gly Cys Tyr;

(SEQ ID NO: 11)
Ala Asp Asp Cys Cys Glu Leu Cys Cys Asn Pro Ala Cys Thr Gly Cys;

(SEQ ID NO: 12)
Ala Asp Asp Cys Cys Glu Tyr Cys Cys Asn Pro Ala Cys Thr Gly Cys;

(SEQ ID NO: 13)
β-Ala Asp Asp Cys Cys Glu Leu Cys Cys Asn Pro Ala Cys Thr Gly Cys;

(SEQ ID NO: 14)
β-Ala Asp Asp Cys Cys Glu Tyr Cys Cys Asn Pro Ala Cys Thr Gly Cys;

(SEQ ID NO: 15)
Ala Asp Asp Cys Cys Glu Leu Cys Cys Asn Pro Ala Cys Thr Gly Cys Tyr;

(SEQ ID NO: 16)
Ala Asp Asp Cys Cys Glu Tyr Cys Cys Asn Pro Ala Cys Thr Gly Cys Tyr;

(SEQ ID NO: 17)
β-Ala Asp Asp Cys Cys Glu Leu Cys Cys Asn Pro Ala Cys Thr Gly Cys Tyr;

(SEQ ID NO: 18)
β-Ala Asp Asp Cys Cys Glu Tyr Cys Cys Asn Pro Ala Cys Thr Gly Cys Tyr;

(SEQ ID NO: 19)
Pro Asp Asp Cys Cys Glu Leu Cys Cys Asn Pro Ala Cys Thr Gly Cys;

(SEQ ID NO: 20)
Pro Asp Asp Cys Cys Glu Tyr Cys Cys Asn Pro Ala Cys Thr Gly Cys;
```

-continued

Pro Asp Asp Cys Cys Glu Leu Cys Cys Asn Pro Ala Cys Thr Gly Cys Tyr;   (SEQ ID NO: 21)

Pro Asp Asp Cys Cys Glu Tyr Cys Cys Asn Pm Ala Cys Thr Gly Cys Tyr;   (SEQ ID NO: 22)

Thr Asp Asp Cys Cys Glu Leu Cys Cys Asn Pro Ala Cys Thr Gly Cys;   (SEQ ID NO: 23)

Thr Asp Asp Cys Cys Glu Tyr Cys Cys Asn Pro Ala Cys Thr Gly Cys;   (SEQ ID NO: 24)

Thr Asp Asp Cys Cys Glu Leu Cys Cys Asn Pro Ala Cys Thr Gly Cys Tyr;   (SEQ ID NO: 25)

Thr Asp Asp Cys Cys Glu Tyr Cys Cys Asn Pro Ala Cys Thr Gly Cys Tyr;   (SEQ ID NO: 26)

Gly Asp Asp Cys Cys Glu Leu Cys Cys Asn Pro Ala Cys Thr Gly Cys;   (SEQ ID NO: 27)

Gly Asp Asp Cys Cys Glu Tyr Cys Cys Asn Pro Ala Cys Thr Gly Cys;   (SEQ ID NO: 28)

Gly Asp Asp Cys Cys Glu Leu Cys Cys Asn Pro Ala Cys Thr Gly Cys Tyr;   (SEQ ID NO: 29)

Gly Asp Asp Cys Cys Glu Tyr Cys Cys Asn Pro Ala Cys Thr Gly Cys Tyr;   (SEQ ID NO: 30)

Asp Asp Asp Cys Cys Glu Leu Cys Cys Asn Pro Ala Cys Thr Gly Cys;   (SEQ ID NO: 31)

Asp Asp Asp Cys Cys Glu Tyr Cys Cys Asn Pro Ala Cys Thr Gly Cys;   (SEQ ID NO: 32)

Asp Asp Asp Cys Cys Glu Leu Cys Cys Asn Pro Ala Cys Thr Gly Cys Tyr;   (SEQ ID NO: 33)

Asp Asp Asp Cys Cys Glu Tyr Cys Cys Asn Pro Ala Cys Thr Gly Cys Tyr;   (SEQ ID NO: 34)

Glu Glu Cys Cys Glu Leu Cys Cys Asn Pro Ala Cys Thr Gly Cys;   (SEQ ID NO: 35)

Glu Glu Cys Cys Glu Tyr Cys Cys Asn Pro Ala Cys Thr Gly Cys;   (SEQ ID NO: 36)

Glu Glu Cys Cys Glu Leu Cys Cys Asn Pro Ala Cys Thr Gly Cys Tyr;   (SEQ ID NO: 37)

Glu Glu Cys Cys Glu Tyr Cys Cys Asn Pro Ala Cys Thr Gly Cys Tyr;   (SEQ ID NO: 38)

Glu Glu Glu Cys Cys Glu Leu Cys Cys Asn Pro Ala Cys Thr Gly Cys;   (SEQ ID NO: 39)

Glu Glu Glu Cys Cys Glu Tyr Cys Cys Asn Pro Ala Cys Thr Gly Cys;   (SEQ ID NO: 40)

Glu Glu Glu Cys Cys Glu Leu Cys Cys Asn Pro Ala Cys Thr Gly Cys Tyr;   (SEQ ID NO: 41)

Glu Glu Glu Cys Cys Glu Tyr Cys Cys Asn Pro Ala Cys Thr Gly Cys Tyr;   (SEQ ID NO: 42)

Glu Asp Cys Cys Glu Leu Cys Cys Asn Pro Ala Cys Thr Gly Cys;   (SEQ ID NO: 43)

Glu Asp Cys Cys Glu Tyr Cys Cys Asn Pro Ala Cys Thr Gly Cys;   (SEQ ID NO: 44)

Glu Asp Cys Cys Glu Leu Cys Cys Asn Pro Ala Cys Thr Gly Cys Tyr;   (SEQ ID NO: 45)
or

Glu Asp Cys Cys Glu Tyr Cys Cys Asn Pro Ala Cys Thr Gly Cys Tyr;   (SEQ ID NO: 46)

wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

In other embodiments, the present invention provides a peptide or pharmaceutically acceptable salt thereof, wherein said peptide comprises:

```
                                                      (SEQ ID NO: 47)
D-Asp Asp Asp Cys Cys Glu Tyr Cys Cys Asn Pro Ala Cys Thr Gly Cys Tyr;

(SEQ ID NO: 48)
D-Ala Asp Asp Cys Cys Glu Tyr Cys Cys Asn Pro Ala Cys Thr Gly Cys Tyr;

(SEQ ID NO: 49)
D-Asn Asp Asp Cys Cys Glu Leu Cys Cys Asn Pro Ala Cys Thr Gly Cys Tyr;

(SEQ ID NO: 50)
D-Ala Asp Asp Cys Cys Glu Leu Cys Cys Asn Pro Ala Cys Thr Gly Cys Tyr;

(SEQ ID NO: 51)
Asp Asp Asp Cys Cys Glu Leu Cys Cys MAs Pro Ala Cys Thr Gly Cys D-Tyr;

(SEQ ID NO: 52)
D-Asp Asp Asp Cys Cys Glu Leu Cys Cys Asn Pro Ala Cys Thr Gly Cys;

(SEQ ID NO: 53)
Asn Asp Asp Cys Cys Glu Tyr Cys Cys Asn Pro Ala Cys Thr Gly Cys Tyr;

(SEQ ID NO: 54)
Asp Asp Cys Cys Glu Tyr Cys Cys Asn Pro Ala Cys Thr Gly Cys Tyr;

(SEQ ID NO: 55)
Asp Asp Asp Cys Cys Glu Tyr Cys Cys Asn Pro Ala Cys Thr Gly Cys Tyr;

(SEQ ID NO: 56)
Gly Asp Asp Cys Cys Glu Tyr Cys Cys Asn Pro Ala Cys Thr Gly Cys Tyr;

(SEQ ID NO: 57)
Pro Asp Asp Cys Cys Glu Tyr Cys Cys Asn Pro Ala Cys Thr Gly Cys Tyr;

(SEQ ID NO: 58)
Ala Asp Asp Cys Cys Glu Tyr Cys Cys Asn Pro Ala Cys Thr Gly Cys Tyr;

(SEQ ID NO: 59)
Asn Asp Asp Cys Cys Glu Leu Cys Cys Asn Pro Ala Cys Thr Gly Cys Tyr;

(SEQ ID NO: 60)
Ala Asp Asp Cys Cys Glu Leu Cys Cys Asn Pro Ala Cys Thr Gly Cys Tyr;

(SEQ ID NO: 61)
β-Ala Asp Asp Cys Cys Glu Leu Cys Cys Asn Pro Ala Cys Thr Gly Cys Tyr;

(SEQ ID NO: 62)
Asp Asp Cys Cys Glu Leu Cys Cys Asn Pro Ala Cys Thr Gly Cys Tyr;

(SEQ ID NO: 63)
Asp Asp Asp Cys Cys Glu Leu Cys Cys Asn Pro Ala Cys Thr Gly Cys Tyr;

(SEQ ID NO: 64)
Pro Asp Asp Cys Cys Glu Leu Cys Cys Asn Pro Ala Cys Thr Gly Cys Tyr;

(SEQ ID NO: 65)
Gly Asp Asp Cys Cys Glu Leu Cys Cys Asn Pro Ala Cys Thr Gly Cys Tyr;

(SEQ ID NO: 66)
Asp Asp Asp Cys Cys Glu Leu Cys Cys Asn Pro Ala Cys Thr Gly Cys;
or (SEQ ID NO: 67)
Glu Glu Glu Cys Cys Glu Tyr Cys Cys Asn Pro Ala Cys Thr Gly Cys Tyr.
```

In some embodiments, the present invention provides a peptide or pharmaceutically acceptable salt thereof, wherein the peptide comprises the amino acid sequence
$Xaa_1\ Asp_2\ Xaa_3\ Cys_4\ Cys_5\ Glu_6\ Xaa_7\ Cys_8\ Cys_9\ Asn_{10}\ Pro_{11}\ Ala_{12}\ Cys_{13}\ Thr_{14}\ Gly_{15}\ Cys_{16}\ Xaa_{17}$ (SEQ ID NO:68); wherein $Xaa_1$ is Asn, D-Asn, Gln, D-Gln, Pro, D-Pro, Ala, β-Ala, D-Ala, Val, D-Val, Gly, Thr, D-Thr, Asp, D-Asp, Glu, or D-Glu;

$Xaa_3$ is Asp or is absent;

$Xaa_7$ is Tyr or Leu; and $Xaa_{17}$ is Tyr or is absent.

In some embodiments, the peptide comprises the amino acid sequence:

```
                                                         (SEQ ID NO: 3)
Asp Asp Cys Cys Glu Leu Cys Cys Asn Pro Ala Cys Thr Gly Cys;

(SEQ ID NO: 4)
Asp Asp Cys Cys Glu Tyr Cys Cys Asn Pro Ala Cys Thr Gly Cys;

(SEQ ID NO: 5)
Asp Asp Cys Cys Glu Leu Cys Cys Asn Pro Ala Cys Thr Gly Cys Tyr;

(SEQ ID NO: 6)
Asp Asp Cys Cys Glu Tyr Cys Cys Asn Pro Ala Cys Thr Gly Cys Tyr;

(SEQ ID NO: 7)
Asn Asp Asp Cys Cys Glu Leu Cys Cys Asn Pro Ala Cys Thr Gly Cys;

(SEQ ID NO: 8)
Asn Asp Asp Cys Cys Glu Tyr Cys Cys Asn Pro Ala Cys Thr Gly Cys;

(SEQ ID NO: 9)
Asn Asp Asp Cys Cys Glu Leu Cys Cys Asn Pro Ala Cys Thr Gly Cys Tyr;

(SEQ ID NO: 10)
Asn Asp Asp Cys Cys Glu Tyr Cys Cys Asn Pro Ala Cys Thr Gly Cys Tyr;

(SEQ ID NO: 11)
Ala Asp Asp Cys Cys Glu Leu Cys Cys Asn Pro Ala Cys Thr Gly Cys;

(SEQ ID NO: 12)
Ala Asp Asp Cys Cys Glu Tyr Cys Cys Asn Pro Ala Cys Thr Gly Cys;

(SEQ ID NO: 13)
β-Ala Asp Asp Cys Cys Glu Leu Cys Cys Asn Pro Ala Cys Thr Gly Cys;

(SEQ ID NO: 14)
β-Ala Asp Asp Cys Cys Glu Tyr Cys Cys Asn Pro Ala Cys Thr Gly Cys;

(SEQ ID NO: 15)
Ala Asp Asp Cys Cys Glu Leu Cys Cys Asn Pro Ala Cys Thr Gly Cys Tyr;

(SEQ ID NO: 16)
Ala Asp Asp Cys Cys Glu Tyr Cys Cys Asn Pro Ala Cys Thr Gly Cys Tyr;

(SEQ ID NO: 17)
β-Ala Asp Asp Cys Cys Glu Leu Cys Cys Asn Pro Ala Cys Thr Gly Cys Tyr;

(SEQ ID NO: 18)
β-Ala Asp Asp Cys Cys Glu Tyr Cys Cys Asn Pro Ala Cys Thr Gly Cys Tyr;

(SEQ ID NO: 19)
Pro Asp Asp Cys Cys Glu Leu Cys Cys Asn Pro Ala Cys Thr Gly Cys;

(SEQ ID NO: 20)
Pro Asp Asp Cys Cys Glu Tyr Cys Cys Asn Pro Ala Cys Thr Gly Cys;

(SEQ ID NO: 21)
Pro Asp Asp Cys Cys Glu Leu Cys Cys Asn Pro Ala Cys Thr Gly Cys Tyr;

(SEQ ID NO: 22)
Pro Asp Asp Cys Cys Glu Tyr Cys Cys Asn Pro Ala Cys Thr Gly Cys Tyr;

(SEQ ID NO: 23)
Thr Asp Asp Cys Cys Glu Leu Cys Cys Asn Pro Ala Cys Thr Gly Cys;

(SEQ ID NO: 24)
Thr Asp Asp Cys Cys Glu Tyr Cys Cys Asn Pro Ala Cys Thr Gly Cys;

(SEQ ID NO: 25)
Thr Asp Asp Cys Cys Glu Leu Cys Cys Asn Pro Ala Cys Thr Gly Cys Tyr;
```

```
                                                        (SEQ ID NO: 26)
Thr Asp Asp Cys Cys Glu Tyr Cys Cys Asn Pro Ala Cys Thr Gly Cys Tyr;

(SEQ ID NO: 27)
Gly Asp Asp Cys Cys Glu Leu Cys Cys Asn Pro Ala Cys Thr Gly Cys;

(SEQ ID NO: 28)
Gly Asp Asp Cys Cys Glu Tyr Cys Cys Asn Pro Ala Cys Thr Gly Cys;

(SEQ ID NO: 29)
Gly Asp Asp Cys Cys Glu Leu Cys Cys Asn Pro Ala Cys Thr Gly Cys Tyr;

(SEQ ID NO: 30)
Gly Asp Asp Cys Cys Glu Tyr Cys Cys Asn Pro Ala Cys Thr Gly Cys Tyr;

(SEQ ID NO: 31)
Asp Asp Asp Cys Cys Glu Leu Cys Cys Asn Pro Ala Cys Thr Gly Cys;

(SEQ ID NO: 32)
Asp Asp Asp Cys Cys Glu Tyr Cys Cys Asn Pro Ala Cys Thr Gly Cys;

(SEQ ID NO: 33)
Asp Asp Asp Cys Cys Glu Leu Cys Cys Asn Pro Ala Cys Thr Gly Cys Tyr;

(SEQ ID NO: 34)
Asp Asp Asp Cys Cys Glu Tyr Cys Cys Asn Pro Ala Cys Thr Gly Cys Tyr;

(SEQ ID NO: 43)
Glu Asp Cys Cys Glu Leu Cys Cys Asn Pro Ala Cys Thr Gly Cys;

(SEQ ID NO: 44)
Glu Asp Cys Cys Glu Tyr Cys Cys Asn Pro Ala Cys Thr Gly Cys;

(SEQ ID NO: 45)
Glu Asp Cys Cys Glu Leu Cys Cys Asn Pro Ala Cys Thr Gly Cys Tyr;
or (SEQ ID NO: 46)
Glu Asp Cys Cys Glu Tyr Cys Cys Asn Pro Ala Cys Thr Gly Cys Tyr;
``` wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

In other embodiments, the peptide comprises no more than 50, 40, 30 or 20 amino acids. For instance, the peptide comprises no more than 19, 18, 17 or 16 amino acids.

In several embodiments, the present invention provides a peptide or pharmaceutically acceptable salt thereof, wherein the peptide consists of the amino acid sequence:

$Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$ (SEQ ID NO:1), or a pharmaceutically acceptable salt thereof; wherein $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, α-aminosuberic acid (Asu), α-aminoadipic acid (Aad), or α-aminopimelic acid (Apm);

$Xaa_2$ is Asp, β-carboxylated Asp, Glu, γ-carboxylated Glu, Asu, Aad, Apm, or is absent;

$Xaa_3$ is Asp, β-carboxylated Asp, Glu, γ-carboxylated Glu, Asu, Aad, Apm, or is absent;

$Xaa_4$ is Cys or D-Cys;

$Xaa_6$ is Asp or Glu;

$Xaa_7$ is Tyr, Leu, Phe or Ile;

$Xaa_8$ is Cys or D-Cys;

$Xaa_{14}$ is Thr, Ala or Phe;

$Xaa_{16}$ is Cys or D-Cys; and $Xaa_{17}$ is Tyr, D-Tyr, or is absent;

wherein:

$Xaa_1$ may be modified on its amino group by methyl, ethanedioic acid, propanedioic acid, butanedioic acid, pentanedioic acid, hexanedioic acid, heptanedioic acid or octanedioic acid; and if both $Xaa_2$ and $Xaa_3$ are absent, then $Xaa_1$ must be β-carboxylated Asp or γ-carboxylated Glu, or $Xaa_1$ must be Asp, D-Asp, Glu, D-Glu, Asu, Aad, Apm and must be modified on its amino group by ethanedioic acid, propanedioic acid, or butanedioic acid, pentanedioic acid, hexanedioic acid, heptanedioic acid or octanedioic acid.

In several embodiments, $Xaa_2$ is Asp or Glu. In others, $Xaa_2$ is Asp.

In several embodiments, $Xaa_2$ and $Xaa_3$ are both present. In several embodiments, $Xaa_2$ is present and $Xaa_3$ is absent. In several embodiments, $Xaa_2$ and $Xaa_3$ are both absent In several embodiments, $Xaa_3$ is Asp or Glu. In others, $Xaa_3$ is Asp.

In several embodiments, either or both of $Xaa_2$ and $Xaa_3$ are present and $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, Asu, Aad or Apm. In further embodiments, $Xaa_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu. In yet further embodiments, $Xaa_1$ is Asp, D-Asp, Glu or D-Glu.

In several embodiments, $Xaa_4$ is Cys.
In several embodiments, $Xaa_6$ is Glu.
In several embodiments, $Xaa_7$ is Tyr or Leu.
In several embodiments, $Xaa_8$ is Cys.
In several embodiments, $Xaa_{14}$ is Thr.
In several embodiments, $Xaa_{16}$ is Cys.
In several embodiments, $Xaa_{17}$ is Tyr.

In several embodiments, Xaa$_{17}$ is absent.

In some embodiments, the present invention provides a peptide or pharmaceutically acceptable salt thereof, wherein said peptide consists of the amino acid sequence Xaa$_1$ Xaa$_2$ Xaa$_3$ Cys$_4$ Cys$_5$ Glu$_6$ Xaa$_7$ Cys$_8$ Cys$_9$ Asn$_{10}$ Pro$_{11}$ Ala$_{12}$ Cys$_{13}$ Thr$_{14}$ Gly$_{15}$ Cys$_{16}$ Xaa$_{17}$ (SEQ ID NO:2);

wherein

Xaa$_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;

Xaa$_2$ is Asp or Glu;

Xaa$_3$ is Asp, Glu, or is absent;

Xaa$_7$ is Tyr or Leu; and

Xaa$_{17}$ is Tyr or is absent.

In some embodiments, the present invention provides a peptide or pharmaceutically acceptable salt thereof, wherein said peptide consists of:

```
                                                       (SEQ ID NO: 3)
Asp Asp Cys Cys Glu Leu Cys Cys Asn Pro Ala Cys Thr Gly Cys;

(SEQ ID NO: 4)
Asp Asp Cys Cys Glu Tyr Cys Cys Asn Pro Ala Cys Thr Gly Cys;

(SEQ ID NO: 5)
Asp Asp Cys Cys Glu Leu Cys Cys Asn Pro Ala Cys Thr Gly Cys Tyr;

(SEQ ID NO: 6)
Asp Asp Cys Cys Glu Tyr Cys Cys Asn Pro Ala Cys Thr Gly Cys Tyr;

(SEQ ID NO: 7)
Asn Asp Asp Cys Cys Glu Leu Cys Cys Asn Pro Ala Cys Thr Gly Cys;

(SEQ ID NO: 8)
Asn Asp Asp Cys Cys Glu Tyr Cys Cys Asn Pro Ala Cys Thr Gly Cys;

(SEQ ID NO: 9)
Asn Asp Asp Cys Cys Glu Leu Cys Cys Asn Pro Ala Cys Thr Gly Cys Tyr;

(SEQ ID NO: 10)
Asn Asp Asp Cys Cys Glu Tyr Cys Cys Asn Pro Ala Cys Thr Gly Cys Tyr;

(SEQ ID NO: 11)
Ala Asp Asp Cys Cys Glu Leu Cys Cys Asn Pro Ala Cys Thr Gly Cys;

(SEQ ID NO: 12)
Ala Asp Asp Cys Cys Glu Tyr Cys Cys Asn Pro Ala Cys Thr Gly Cys;

(SEQ ID NO: 13)
β-Ala Asp Asp Cys Cys Glu Leu Cys Cys Asn Pro Ala Cys Thr Gly Cys;

(SEQ ID NO: 14)
β-Ala Asp Asp Cys Cys Glu Tyr Cys Cys Asn Pro Ala Cys Thr Gly Cys;

(SEQ ID NO: 15)
Ala Asp Asp Cys Cys Glu Leu Cys Cys Asn Pro Ala Cys Thr Gly Cys Tyr;

(SEQ ID NO: 16)
Ala Asp Asp Cys Cys Glu Tyr Cys Cys Asn Pro Ala Cys Thr Gly Cys Tyr;

(SEQ ID NO: 17)
β-Ala Asp Asp Cys Cys Glu Leu Cys Cys Asn Pro Ala Cys Thr Gly Cys Tyr;

(SEQ ID NO: 18)
β-Ala Asp Asp Cys Cys Glu Tyr Cys Cys Asn Pro Ala Cys Thr Gly Cys Tyr;

(SEQ ID NO: 19)
Pro Asp Asp Cys Cys Glu Leu Cys Cys Asn Pro Ala Cys Thr Gly Cys;

(SEQ ID NO: 20)
Pro Asp Asp Cys Cys Glu Tyr Cys Cys Asn Pro Ala Cys Thr Gly Cys;

(SEQ ID NO: 21)
Pro Asp Asp Cys Cys Glu Leu Cys Cys Asn Pro Ala Cys Thr Gly Cys Tyr;

(SEQ ID NO: 22)
Pro Asp Asp Cys Cys Glu Tyr Cys Cys Asn Pro Ala Cys Thr Gly Cys Tyr;

(SEQ ID NO: 23)
Thr Asp Asp Cys Cys Glu Leu Cys Cys Asn Pro Ala Cys Thr Gly Cys;

(SEQ ID NO: 24)
Thr Asp Asp Cys Cys Glu Tyr Cys Cys Asn Pro Ala Cys Thr Gly Cys;
```

```
                                                                    (SEQ ID NO: 25)
Thr Asp Asp Cys Cys Glu Leu Cys Cys Asn Pro Ala Cys Thr Gly Cys Tyr;

(SEQ ID NO: 26)
Thr Asp Asp Cys Cys Glu Tyr Cys Cys Asn Pro Ala Cys Thr Gly Cys Tyr;

(SEQ ID NO: 27)
Gly Asp Asp Cys Cys Glu Leu Cys Cys Asn Pro Ala Cys Thr Gly Cys;

(SEQ ID NO: 28)
Gly Asp Asp Cys Cys Glu Tyr Cys Cys Asn Pro Ala Cys Thr Gly Cys;

(SEQ ID NO: 29)
Gly Asp Asp Cys Cys Glu Leu Cys Cys Asn Pro Ala Cys Thr Gly Cys Tyr;

(SEQ ID NO: 30)
Gly Asp Asp Cys Cys Glu Tyr Cys Cys Asn Pro Ala Cys Thr Gly Cys Tyr;

(SEQ ID NO: 31)
Asp Asp Asp Cys Cys Glu Leu Cys Cys Asn Pro Ala Cys Thr Gly Cys;

(SEQ ID NO: 32)
Asp Asp Asp Cys Cys Glu Tyr Cys Cys Asn Pro Ala Cys Thr Gly Cys;

(SEQ ID NO: 33)
Asp Asp Asp Cys Cys Glu Leu Cys Cys Asn Pro Ala Cys Thr Gly Cys Tyr;

(SEQ ID NO: 34)
Asp Asp Asp Cys Cys Glu Tyr Cys Cys Asn Pro Ala Cys Thr Gly Cys Tyr;

(SEQ ID NO: 35)
Glu Glu Cys Cys Glu Leu Cys Cys Asn Pro Ala Cys Thr Gly Cys;

(SEQ ID NO: 36)
Glu Glu Cys Cys Glu Tyr Cys Cys Asn Pro Ala Cys Thr Gly Cys;

(SEQ ID NO: 37)
Glu Glu Cys Cys Glu Leu Cys Cys Asn Pro Ala Cys Thr Gly Cys Tyr;

(SEQ ID NO: 38)
Glu Glu Cys Cys Glu Tyr Cys Cys Asn Pro Ala Cys Thr Gly Cys Tyr;

(SEQ ID NO: 39)
Glu Glu Glu Cys Cys Glu Leu Cys Cys Asn Pro Ala Cys Thr Gly Cys;

(SEQ ID NO: 40)
Glu Glu Glu Cys Cys Glu Tyr Cys Cys Asn Pro Ala Cys Thr Gly Cys;

(SEQ ID NO: 41)
Glu Glu Glu Cys Cys Glu Leu Cys Cys Asn Pro Ala Cys Thr Gly Cys Tyr;

(SEQ ID NO: 42)
Glu Glu Glu Cys Cys Glu Tyr Cys Cys Asn Pro Ala Cys Thr Gly Cys Tyr;

(SEQ ID NO: 43)
Glu Asp Cys Cys Glu Leu Cys Cys Asn Pro Ala Cys Thr Gly Cys;

(SEQ ID NO: 44)
Glu Asp Cys Cys Glu Tyr Cys Cys Asn Pro Ala Cys Thr Gly Cys;

(SEQ ID NO: 45)
Glu Asp Cys Cys Glu Leu Cys Cys Asn Pro Ala Cys Thr Gly Cys Tyr;
or (SEQ ID NO: 46)
Glu Asp Cys Cys Glu Tyr Cys Cys Asn Pro Ala Cys Thr Gly Cys Tyr;
``` wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

In other embodiments, the present invention provides a peptide or pharmaceutically acceptable salt thereof, wherein said peptide consists of:

```
                                              (SEQ ID NO: 47)
D-Asp Asp Asp Cys Cys Glu Tyr Cys Cys Asn Pro Ala Cys Thr Gly Cys Tyr;

(SEQ ID NO: 48)
D-Ala Asp Asp Cys Cys Glu Tyr Cys Cys Asn Pro Ala Cys Thr Gly Cys Tyr;

(SEQ ID NO: 49)
D-Asn Asp Asp Cys Cys Glu Leu Cys Cys Asn Pro Ala Cys Thr Gly Cys Tyr;

(SEQ ID NO: 50)
D-Ala Asp Asp Cys Cys Glu Leu Cys Cys Asn Pro Ala Cys Thr Gly Cys Tyr;

(SEQ ID NO: 51)
Asp Asp Asp Cys Cys Glu Leu Cys Cys Asn Pro Ala Cys Thr Gly Cys D-Tyr;

(SEQ ID NO: 52)
D-Asp Asp Asp Cys Cys Glu Leu Cys Cys Asn Pro Ala Cys Thr Gly Cys;

(SEQ ID NO: 53)
Asn Asp Asp Cys Cys Glu Tyr Cys Cys Asn Pro Ala Cys Thr Gly Cys Tyr;

(SEQ ID NO: 54)
Asp Asp Cys Cys Glu Tyr Cys Cys Asn Pro Ala Cys Thr Gly Cys Tyr;

(SEQ ID NO: 55)
Asp Asp Asp Cys Cys Glu Tyr Cys Cys Asn Pro Ala Cys Thr Gly Cys Tyr;

(SEQ ID NO: 56)
Gly Asp Asp Cys Cys Glu Tyr Cys Cys Asn Pro Ala Cys Thr Gly Cys Tyr;

(SEQ ID NO: 57)
Pro Asp Asp Cys Cys Glu Tyr Cys Cys Asn Pro Ala Cys Thr Gly Cys Tyr;

(SEQ ID NO: 58)
Ala Asp Asp Cys Cys Glu Tyr Cys Cys Asn Pro Ala Cys Thr Gly Cys Tyr;

(SEQ ID NO: 59)
Asn Asp Asp Cys Cys Glu Leu Cys Cys Asn Pro Ala Cys Thr Gly Cys Tyr;

(SEQ ID NO: 60)
Ala Asp Asp Cys Cys Glu Leu Cys Cys Asn Pro Ala Cys Thr Gly Cys Tyr;

(SEQ ID NO: 61)
β-Ala Asp Asp Cys Cys Glu Leu Cys Cys Asn Pro Ala Cys Thr Gly Cys Tyr;

(SEQ ID NO: 62)
Asp Asp Cys Cys Glu Leu Cys Cys Asn Pro Ala Cys Thr Gly Cys Tyr;

(SEQ ID NO: 63)
Asp Asp Asp Cys Cys Glu Leu Cys Cys Asn Pro Ala Cys Thr Gly Cys Tyr;

(SEQ ID NO: 64)
Pro Asp Asp Cys Cys Glu Leu Cys Cys Asn Pro Ala Cys Thr Gly Cys Tyr;

(SEQ ID NO: 65)
Gly Asp Asp Cys Cys Glu Leu Cys Cys Asn Pro Ala Cys Thr Gly Cys Tyr;

(SEQ ID NO: 66)
Asp Asp Asp Cys Cys Glu Leu Cys Cys Asn Pro Ala Cys Thr Gly Cys;
or (SEQ ID NO: 67)
Glu Glu Glu Cys Cys Glu Tyr Cys Cys Asn Pro Ala Cys Thr Gly Cys Tyr;
```

In some embodiments, the present invention provides a peptide or pharmaceutically acceptable salt thereof, wherein the peptide consists of the amino acid sequence $Xaa_1\ Asp_2\ Xaa_3 Cys_4\ Cys_5\ Glu_6\ Xaa_7\ Cys_8\ Cys_9\ Asn_{10}\ Pro_{11}\ Ala_{12}\ Cys_{13}\ Thr_{14}\ Gly_{15}\ Cys_{16}\ Xaa_{17}$ (SEQ ID NO. 68);

wherein
$Xaa_1$ is Asn, D-Asn, Gln, D-Gln, Pro, D-Pro, Ala, β-Ala, D-Ala, Val, D-Val, Gly, Thr, D-Thr, Asp, D-Asp, Glu, or D-Glu;
$Xaa_3$ is Asp or is absent;
$Xaa_7$ is Tyr or Leu; and
$Xaa_{17}$ is Tyr or is absent.

In some embodiments, the peptide consists of the amino acid sequence:

```
                                                    (SEQ ID NO: 3)
Asp Asp Cys Cys Glu Leu Cys Cys Asn Pro Ala Cys Thr Gly Cys;

(SEQ ID NO: 4)
Asp Asp Cys Cys Glu Tyr Cys Cys Asn Pro Ala Cys Thr Gly Cys;

(SEQ ID NO: 5)
Asp Asp Cys Cys Glu Leu Cys Cys Asn Pro Ala Cys Thr Gly Cys Tyr;

(SEQ ID NO: 6)
Asp Asp Cys Cys Glu Tyr Cys Cys Asn Pro Ala Cys Thr Gly Cys Tyr;

(SEQ ID NO: 7)
Asn Asp Asp Cys Cys Glu Leu Cys Cys Asn Pro Ala Cys Thr Gly Cys;

(SEQ ID NO: 8)
Asn Asp Asp Cys Cys Glu Tyr Cys Cys Asn Pro Ala Cys Thr Gly Cys;

(SEQ ID NO: 9)
Asn Asp Asp Cys Cys Glu Leu Cys Cys Asn Pro Ala Cys Thr Gly Cys Tyr;

(SEQ ID NO: 10)
Asn Asp Asp Cys Cys Glu Tyr Cys Cys Asn Pro Ala Cys Thr Gly Cys Tyr;

(SEQ ID NO: 11)
Ala Asp Asp Cys Cys Glu Leu Cys Cys Asn Pro Ala Cys Thr Gly Cys;

(SEQ ID NO: 12)
Ala Asp Asp Cys Cys Glu Tyr Cys Cys Asn Pro Ala Cys Thr Gly Cys;

(SEQ ID NO: 13)
β-Ala Asp Asp Cys Cys Glu Leu Cys Cys Asn Pro Ala Cys Thr Gly Cys;

(SEQ ID NO: 14)
β-Ala Asp Asp Cys Cys Glu Tyr Cys Cys Asn Pro Ala Cys Thr Gly Cys;

(SEQ ID NO: 15)
Ala Asp Asp Cys Cys Glu Leu Cys Cys Asn Pro Ala Cys Thr Gly Cys Tyr;

(SEQ ID NO: 16)
Ala Asp Asp Cys Cys Glu Tyr Cys Cys Asn Pro Ala Cys Thr Gly Cys Tyr;

(SEQ ID NO: 17)
β-Ala Asp Asp Cys Cys Glu Leu Cys Cys Asn Pro Ala Cys Thr Gly Cys Tyr;

(SEQ ID NO: 18)
β-Ala Asp Asp Cys Cys Glu Tyr Cys Cys Asn Pro Ala Cys Thr Gly Cys Tyr;

(SEQ ID NO: 19)
Pro Asp Asp Cys Cys Glu Leu Cys Cys Asn Pro Ala Cys Thr Gly Cys;

(SEQ ID NO: 20)
Pro Asp Asp Cys Cys Glu Tyr Cys Cys Asn Pro Ala Cys Thr Gly Cys;

(SEQ ID NO: 21)
Pro Asp Asp Cys Cys Glu Leu Cys Cys Asn Pro Ala Cys Thr Gly Cys Tyr;

(SEQ ID NO: 22)
Pro Asp Asp Cys Cys Glu Tyr Cys Cys Asn Pro Ala Cys Thr Gly Cys Tyr;

(SEQ ID NO: 23)
Thr Asp Asp Cys Cys Glu Leu Cys Cys Asn Pro Ala Cys Thr Gly Cys;

(SEQ ID NO: 24)
Thr Asp Asp Cys Cys Glu Tyr Cys Cys Asn Pro Ala Cys Thr Gly Cys;
```

```
                                                         (SEQ ID NO: 25)
Thr Asp Asp Cys Cys Glu Leu Cys Cys Asn Pro Ala Cys Thr Gly Cys Tyr;

(SEQ ID NO: 26)
Thr Asp Asp Cys Cys Glu Tyr Cys Cys Asn Pro Ala Cys Thr Gly Cys Tyr;

(SEQ ID NO: 27)
Gly Asp Asp Cys Cys Glu Leu Cys Cys Asn Pro Ala Cys Thr Gly Cys;

(SEQ ID NO: 28)
Gly Asp Asp Cys Cys Glu Tyr Cys Cys Asn Pro Ala Cys Thr Gly Cys;

(SEQ ID NO: 29)
Gly Asp Asp Cys Cys Glu Leu Cys Cys Asn Pro Ala Cys Thr Gly Cys Tyr;

(SEQ ID NO: 30)
Gly Asp Asp Cys Cys Glu Tyr Cys Cys Asn Pro Ala Cys Thr Gly Cys Tyr;

(SEQ ID NO: 31)
Asp Asp Asp Cys Cys Glu Leu Cys Cys Asn Pro Ala Cys Thr Gly Cys;

(SEQ ID NO: 32)
Asp Asp Asp Cys Cys Glu Tyr Cys Cys Asn Pro Ala Cys Thr Gly Cys;

(SEQ ID NO: 33)
Asp Asp Asp Cys Cys Glu Leu Cys Cys Asn Pro Ala Cys Thr Gly Cys Tyr;

(SEQ ID NO: 34)
Asp Asp Asp Cys Cys Glu Tyr Cys Cys Asn Pro Ala Cys Thr Gly Cys Tyr;

(SEQ ID NO: 43)
Glu Asp Cys Cys Glu Leu Cys Cys Asn Pro Ala Cys Thr Gly Cys;

(SEQ ID NO: 44)
Glu Asp Cys Cys Glu Tyr Cys Cys Asn Pro Ala Cys Thr Gly Cys;

(SEQ ID NO: 45)
Glu Asp Cys Cys Glu Leu Cys Cys Asn Pro Ala Cys Thr Gly Cys Tyr;
or
                                                         (SEQ ID NO: 46)
Glu Asp Cys Cys Glu Tyr Cys Cys Asn Pro Ala Cys Thr Gly Cys Tyr;
``` wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

In some instances, the peptide is isolated. In others, the peptide is purified.

In some embodiments, a pharmaceutically acceptable salt of the peptide is provided. In some instances, the pharmaceutically acceptable salt is a chloride salt.

Variant Peptides

In some circumstances it can be desirable to treat patients with a variant peptide that binds to and activates intestinal GC-C receptors, but is less active or more active than the non-variant form of the peptide. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

In some peptides one or both members of one or both pairs of Cys residues which normally form a disulfide bond can be replaced by homocysteine, penicillamine, 3-mercaptoproline (Kolodziej et al. 1996 *Int J Pept Protein Res* 48:274); β, β-dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds. In other embodiments, the disulfide bonds may be replaced by hydrocarbon crosslinking (Schafmeister et al. 2000 *J Am Chem Soc* 122: 5891, Patgiri et al. 2008 *Acc Chem Res* 41:1289, Henchey et al. 2008 *Curr Opin Chem Biol* 12:692).

Production of Peptides

In one embodiment, peptides or precursor peptides of the invention can be produced recombinantly in any known protein expression system, including, without limitation, bacteria (e.g., *E. coli* or *Bacillus subtilis*), insect cell systems (e.g., *Drosophila* Sf9 cell systems), yeast cell systems (e.g., *S. cerevisiae, S. saccharomyces*) or filamentous fungal expression systems, or animal cell expression systems (e.g., mammalian cell expression systems). Peptides or precursor peptides of the invention may also be chemically synthesized.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally occurring bacterial ST peptide. The secreted, mature peptide can be purified from the culture medium.

The sequence encoding a peptide described herein is can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium.

Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

In other embodiments, peptides containing amino acids not normally incorporated by the translation machinery and described above (e.g., β-carboxylated Asp, γ-carboxylated Glu, Asu, Aad and Apm) may be recombinantly produced by tRNA modification methods. Methods for modifying tRNA including, but not limited to, modifying the anti-codon, the amino acid attachment site, and/or the accepter stem to allow incorporation of unnatural and/or arbitrary amino acids are known in the art (*Biochem. Biophys. Res. Comm.* (2008) 372: 480-485; *Chem. Biol.* (2009) 16:323-36; *Nat. Methods* (2007) 4:239-44; *Nat. Rev. Mol. Cell. Biol.* (2006) 7:775-82; *Methods* (2005) 36:227-238; *Methods* (2005) 36:270-278; *Annu. Rev. Biochem.* (2004) 73:147-176; *Nuc. Acids Res.* (2004) 32:6200-6211; *Proc. Natl. Acad. Sci. USA* (2003) 100:6353-6357; *Royal Soc. Chem.* (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotrityl or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cys); tert-butyl (γ-carboxyl of glutamic acid and the hydroxyl group of threonine, if present); and trityl (β-amid function of the asparagine side chain and the phenolic group of tyrosine, if present). Coupling can be effected with DIC and HOBt in the presence of a tertiary amine, and the peptide can be deprotected and cleaved from the solid support using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent.

Disulfide bonds between Cys residues can be formed using dimethyl sulfoxide (Tam et al. (1991) *J. Am. Chem. Soc.* 113:6657-62) or using an air oxidation strategy. The resulting peptide can be purified by reverse-phase chromatography and lyophilized.

Peptides can be made, isolated or used either in form of the base or as pharmaceutically acceptable salts thereof. Examples of salts include, without limitation, acetate, chloride, sulfate and phosphate salts of the peptide.

Compositions of Peptides and GC-C Receptor Agonists

In another aspect, compositions are provided wherein the peptides, alone or in combination, can be combined with any pharmaceutically acceptable carrier or medium. The peptides can be combined with materials that do not produce an adverse, allergic or otherwise unwanted reaction when administered to a patient. The carriers or media used can include solvents, dispersants, coatings, absorption promoting agents, controlled release agents, and one or more inert excipients (which include starches, polyols, granulating agents, microfilm cellulose, microcrystalline cellulose (e.g., celphere, Celphere Beads®), diluents, lubricants, binders, disintegrating agents, and the like), etc. If desired, tablet dosages of the disclosed compositions may be coated by standard aqueous or nonaqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, powdered cellulose, microfine cellulose, microcrystalline cellulose (e.g., AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

Examples of binders that may be particularly used in pharmaceutical compositions include polyvinyl alcohol, polyvinylpyrrolidone (povidone), a starch, maltodextrin or a cellulose ether (such as, for example, methylcellulose, ethylcellulose, carboxymethylcellulose, hydroxyethyl cellulose, hydroxyethyl methylcellulose, hydroxypropyl cellulose and hydroxypropyl methylcellulose).

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), microfine cellulose, powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g., Aquacoat Ethylcellulose Aqueous Dispersion, 15% w/w, FMC Biopolymer, ECD-30), Eudragit (e.g., Eudragit E PO PE-EL, Roehm Pharma Polymers) and Opadry (e.g., Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g., lipids, sodium cholate, acylcarnitine, salicylates, mixed bile salts, fatty acid micelles, chelators, fatty acid, surfactants, medium chain glycerides), protease inhibitors (e.g., soybean trypsin inhibitor, organic acids), pH-lowering agents and absorption enhancers effective to promote bioavailability (including but not limited to those described in U.S. Pat. Nos. 6,086,918 and 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD& C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, mannitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more stabilizing agents selected from $Mg^{2+}$, $Ca^{2+}$, $Zn^{2+}$, $Mn^{2+}$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof. In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the stabilizing agent is a sterically hindered primary amine. In a further embodiment, the sterically hindered primary amine is an amino acid. In yet a further embodiment, the amino acid is a naturally occurring amino acid. In a still further embodiment, the naturally occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In a still further embodiment, the naturally-occurring amino acid is leucine. In another embodiment, the sterically hindered primary amine is a non-naturally occurring amino acid (e.g., 1-aminocyclohexane carboxylic acid, lanthanine, or theanine). In a further embodiment, the sterically hindered primary amine is cyclohexylamine, 2-methylbutylamine or a polymeric amine such as chitosan. In another embodiment, one or more sterically hindered primary amines may be used in a composition.

In some cases, the sterically hindered primary amine has the formula:

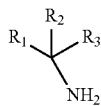

wherein $R_1$, $R_2$ and $R_3$ are independently selected from: H, C(O)OH, $C_1$-$C_6$ alkyl, $C_1$-$C_6$ alkylether, $C_1$-$C_6$ alkylthioether, $C_1$-$C_6$ alkyl carboxylic acid, $C_1$-$C_6$ alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the pharmaceutical composition further comprises a pharmaceutically acceptable binder and/or a pharmaceutically acceptable glidant, lubricant or additive that acts as both a glidant and lubricant and/or an antioxidant. In some embodiments, the pharmaceutical composition is applied to a carrier. In some embodiments, the carrier is a filler.

In some cases the molar ratio of cation:sterically hindered primary amine:peptide in the aqueous solution applied to the carrier is 5-100:5-50:1. In some cases, the molar ratio of cation:sterically hindered primary amine may be equal to or greater than 2:1 (e.g., between 5:1 and 2:1). Thus, in some cases the molar ratio of cation:sterically hindered primary amine: peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1%, 1.5%, or 0.7%).

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by *Remington's Pharmaceutical Sciences* (18th Edition, Mack Publishing Company, 1995).

For treatment of gastrointestinal disorders, the peptides described herein are preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Methods of Treatment

In some embodiments of the invention, a method of treatment is provided for gastrointestinal disorders.

In some embodiments, the gastrointestinal disorder is an upper GI disorder. In a further embodiment, the disorder is GP, post-operative gastric ileus, a functional esophageal disorder, a functional gastroduodenal disorder, gastroesophageal reflux disease (GERD), celiac disease, mucositis, or a duodenal or stomach ulcer.

In some embodiments, the gastrointestinal disorder is GP. In further embodiments, the GP is idiopathic, diabetic or post-surgical GP.

In some embodiments, the gastrointestinal disorder is postoperative gastric ileus.

In some embodiments, the gastrointestinal disorder is a functional esophageal disorder.

In some embodiments, the functional esophageal disorder is functional heartburn, functional chest pain of presumed esophageal origin, functional dysphagia or globus.

In some embodiments, the gastrointestinal disorder is a functional gastroduodenal disorder.

In some embodiments, the functional gastroduodenal disorder is FD, a belching disorder, a nausea or vomiting disorder, or rumination syndrome. In a further embodiment, the functional gastroduodenal disorder is FD. In some embodiments, the FD is postprandial distress syndrome or epigastric pain syndrome. In some embodiments, the belching disorder is aerophagia or unspecified excessive belching. In some embodiments, the nausea or vomiting disorder is chronic idiopathic nausea, functional vomiting or cyclic vomiting syndrome.

In some embodiments, the gastrointestinal disorder is gastroesophageal reflux disease (GERD).

In some embodiments, the gastrointestinal disorder is celiac disease.

In some embodiments, the gastrointestinal disorder is mucositis.

In some embodiments, the gastrointestinal disorder is a duodenal or stomach ulcer.

The peptides and agonists described herein can be used alone or in combination therapy for the treatment, prevention or reduction of visceral pain associated with a gastrointestinal disorder or pain associated with another disorder as described herein.

The GC-C receptor agonists described herein can be administered in combination with other agents. For example, the peptides can be administered with an analgesic peptide or compound. The analgesic peptide or compound can be covalently attached to a peptide described herein or it can be a separate agent that is administered together with or sequentially with a peptide described herein in a combination therapy. The GC-C receptor agonists described herein may also be administered in combination with other agents used to treat upper GI disorders including antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod [Zelnorm®], mosapride, zacopride, cisapride, renzapride, prucalopride [Resolor®], benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-La Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), mixed and selective dopamine receptor antagonists (e.g., metoclopramide, itopride, domperidone), vanilloid and cannabinoid receptor agonists, sialorphin and sialorphin-related peptides. Analgesic agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®). Examples of H2 receptor blockers include, without limitation, including cimetidine, ranitidine, famotidine and nizatidine. Examples of acid pump antagonists include, without limitation, revaprazan, CS-526 (*J. Pharmacol. Exp. Ther*. (2007) 323:308-317), PF-03716556 (*J. Pharmacol. Exp. Ther*. (2009) 328(2):671-9), and YH1885 (*Drug Metab. Dispos*. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine cross-linked with epichlorohydrin, dialkylaminoalkyl derivatives of a cross-linked dextran, and N-(cycloalkyl)alkylamines.

Examples of mucosal protecting agents include, without limitation, sucralfate (Carafate), teprenone, polaprezinc, cetraxate and bismuth subsalicyclate.

Combination therapy can be achieved by administering two or more agents, e.g., a GC-C receptor agonist described herein and another therapeutic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, or 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Dosage

The dose range for adult humans may be generally from 5 μg to 100 mg/day orally of the GC-C peptide agonist described herein. Tablets, capsules, or other forms of presentation provided in discrete units may conveniently contain an amount of compound described herein that is effective at such dosage or as a multiple of the same, for instance, units containing 25 μg to 2 mg or around 100 μg to 1 mg. The precise amount of compound prescribed to a patient will be the responsibility of the attendant physician. However, the dose employed will depend on a number of factors, including the age and sex of the patient, the precise disorder being treated, and its severity.

In various embodiments, the dosage unit is administered with food at any time of the day, without food at any time of the day, with food after an overnight fast (e.g., with breakfast), at bedtime after a low fat snack. In one particular embodiment, the dosage unit is administered prior to or subsequent to food consumption (e.g., a meal). In a further embodiment, the dosage unit is administered approximately 15 minutes to 1 hour prior to food consumption. In various embodiments, the dosage unit is administered once a day, twice a day, three times a day, four times a day, five times a day or six times a day. In certain embodiments the dosage unit and daily dose are equivalent.

In combination therapy embodiments of the present invention, the precise amount of each of the two or more active ingredients in a dosage unit will depend on the desired dosage of each component. Thus, it can be useful to create a dosage unit that will, when administered according to a particular dosage schedule (e.g., a dosage schedule specifying a certain number of units and a particular timing for administration), deliver the same dosage of each component as would be administered if the patient was being treated with only a single component. In other circumstances, it might be desirable to create a dosage unit that will deliver a dosage of one or more components that is less than that which would be administered if the patient was being treated only with a single component. Finally, it might be desirable to create a dosage unit that will deliver a dosage of one or more components that is greater than that which would be administered if the patient was being treated only with a single component.

The pharmaceutical composition can include additional ingredients including but not limited to the active ingredients and excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein were prepared by solid phase chemical synthesis and natural folding (air oxidation) by American Peptide Company (Sunnyvale, Calif.). The peptides and their sequences are shown below (wherein the amino acid sequence is the standard one letter code and "dD" refers to D-Asp, "dA" refers to D-Ala, "dY" refers to D-Tyr, "dN" refers to D-Asn and "βA" refers to beta-Ala):

| Peptide Name | Amino Acid Sequence | ID |
|---|---|---|
| Peptide 1 | CCELCCNPACTGCY | (SEQ ID NO: 69) |
| Peptide 2 | CCEFCCNPACTGCY | (SEQ ID NO: 70) |
| Peptide 3 | NDDCCEYCCNPACTGCY | (SEQ ID NO: 53) |
| Peptide 4 | DDCCEYCCNPACTGCY | (SEQ ID NO: 54) |
| Peptide 5 | DDDCCEYCCNPACTGCY | (SEQ ID NO: 55) |
| Peptide 6 | dDDDCCEYCCNPACTGCY | (SEQ ID NO: 47) |
| Peptide 7 | GDDCCEYCCNPACTGCY | (SEQ ID NO: 56) |
| Peptide 8 | PDDCCEYCCNPACTGCY | (SEQ ID NO: 57) |
| Peptide 9 | ADDCCEYCCNPACTGCY | (SEQ ID NO: 58) |
| Peptide 10 | dADDCCEYCCNPACTGCY | (SEQ ID NO: 48) |
| Peptide 11 | NDDCCELCCNPACTGCY | (SEQ ID NO: 59) |
| Peptide 12 | dNDDCCELCCNPACTGCY | (SEQ ID NO: 49) |
| Peptide 13 | ADDCCELCCNPACTGCY | (SEQ ID NO: 60) |
| Peptide 14 | dADDCCELCCNPACTGCY | (SEQ ID NO: 50) |
| Peptide 15 | βADDCCELCCNPACTGCY | (SEQ ID NO: 61) |
| Peptide 16 | DDCCELCCNPACTGCY | (SEQ ID NO: 62) |
| Peptide 17 | DDDCCELCCNPACTGCY | (SEQ ID NO: 63) |

-continued

| Peptide Name | Amino Acid Sequence | ID |
|---|---|---|
| Peptide 18 | PDDCCELCCNPACTGCY | (SEQ ID NO: 64) |
| Peptide 19 | GDDCCELCCNPACTGCY | (SEQ ID NO: 65) |
| Peptide 20 | DDDCCELCCNPACTGC | (SEQ ID NO: 66) |
| Peptide 21 | DDDCCELCCNPACTGCdY | (SEQ ID NO: 51) |
| Peptide 22 | EEECCEYCCNPACTGCY | (SEQ ID NO: 67) |
| Peptide 23 | dDDDCCELCCNPACTGC | (SEQ ID NO: 52) |

Example 1 cGMP Accumulation in T84 Cells for Analysis of GC-C Activity cGMP accumulation in T84 cells was analyzed for GC-C activity. For the cGMP assay, $4.5 \times 10^5$ cells/mL of T84 cells were grown overnight in 24-well tissue culture plates. On the next day, the T84 cells were washed twice with 1 mL of DMEM+20 mM MES (pH 5) or DMEM+50 mM sodium bicarbonate (NaBicarb, pH 8) in which these buffers did not contain serum. After the second wash, the cells were incubated with 450 μL of 1 mM isobutylmethylxanthine (IBMX) in either the pH 5 or pH 8 buffers for 10 minutes at 37° C. to inhibit any phosphodiesterase activity. The peptides were then diluted in either pH 5 or pH 8 buffer to a 10× concentration. The peptide solution of 50 μL was diluted to a final volume of 500 μL with the T84 cells, bringing each peptide concentration to 1x. An eleven-point curve analysis was conducted for each peptide at the final peptide concentrations tested in each assay (in nM): 10000, 3000, 1000, 300, 100, 30, 10, 3, 1, 0.3, 0.1.

There was no peptide control used to determine endogenous levels of cGMP. Peptides were incubated for 30 minutes at 37° C. After 30 minutes, the supernatants were removed and the cells were lysed with 0.1 M HCl, for 30 mins on ice. After 30 minutes, lysates were pipetted off and placed into a 96-well HPLC plate and spun at 10,000 g for 10 minutes to remove any cell debris. Supernatants from the previous spin were removed and placed into a fresh 96-well HPLC plate. Samples were diluted with an equal volume of 1 M ammonium acetate (pH 7) to neutralize samples for better chromatography. A 2×cGMP standard curve was prepared in 0.1 M HCl and then diluted with an equal volume of 1 M ammonium acetate, with the following final concentrations (in nM): 1024, 512, 256, 128, 64, 32, 16, 8, 4, 2, 1.

cGMP concentrations were determined from each sample using the LC/MS conditions (Table 1 below) and the calculated standard curve. $EC_{50}$ values were calculated from concentration-response curves generated with GraphPad Prism Software.

TABLE 1

| LC/MS Conditions | | | | | |
|---|---|---|---|---|---|
| MS: | Thermo Quantum | | | | |
| Ion Mode: | ESI+ | | | | |
| Scan Type: | MRM | | | | |
| Compound: | Transition | Dwell Time (msec) | Collision Energy (V) | Tube Lens | Retention Time (min) |
| cGMP | 346 > 152 | 100 | 28 | 139 | 1.0 |
| HPLC: | Agilent Technologies 1200 Series with CTC Analytics HTS PAL | | | | |
| Column: | Thermo Hypersil Gold 2.1 × 50 mm 5 micron particle size | | | | |
| Flow Rate: | 400 uL/min | | | | |
| Column Temperature: | RT | | | | |
| Autosampler Temperature: | 6° C. | | | | |
| Injection Volume: | 20 uL | | | | |
| Mobile Phases: | A = 98:2 Water:Acetonitrile + 0.1% Formic Acid | | | | |
| | B = 2:98 Water:Acetonitrile + 0.1% Formic Acid | | | | |
| Gradient: | Time (min) | % A | % B | | |
| | 0 | 100 | 0 | | |
| | 0.3 | 30 | 70 | | |
| | 2.00 | 30 | 70 | | |
| | 2.01 | 100 | 0 | | |
| | 4 | 100 | 0 | | |

Effect of pH on cGMP Production

The ability of the GC-C agonist peptides to stimulate cGMP synthesis in human T84 cells at pH 5 and pH 8 was compared. FIG. 1 shows the effect on T84 cGMP dose response for Peptide 1 and Peptide 17. Table 2 lists exemplary peptides of the present invention tested, with the summary of the $EC_{50}$ values for each peptide at pH 5 and pH 8. The ratio of the $EC_{50}$ at pH 8 and pH 5 for each peptide is also provided.

TABLE 2 cGMP response in T84 cells

| | $EC_{50}$ nM | | Ratio $EC_{50}$ pH 8/ $EC_{50}$ pH 5 |
|---|---|---|---|
| Peptide | pH 5 | pH 8 | |
| Peptide 1 | 13.4 | 114 | 8.5 |
| Peptide 2 | 74.4 | 982 | 13.2 |
| Peptide 3 | 170 | 4310 | 25.3 |
| Peptide 4 | 50.4 | 2417 | 48.0 |
| Peptide 5 | 66.5 | 17030 | 256 |
| Peptide 6 | 73.4 | 10740 | 146 |
| Peptide 7 | 51.3 | 19670 | 383 |
| Peptide 8 | 83.4 | 4858 | 58.2 |
| Peptide 9 | 124 | 9893 | 79.8 |
| Peptide 10 | 72.2 | 5513 | 76.4 |
| Peptide 11 | 154 | 424 | 2.7 |
| Peptide 12 | 8.9 | 855 | 96.1 |
| Peptide 13 | 10.7 | 669 | 62.5 |
| Peptide 14 | 6.9 | 1147 | 166.2 |
| Peptide 15 | 6 | 661 | 110.2 |
| Peptide 16 | 9.9 | 266 | 26.9 |
| Peptide 17 | 12.9 | 4983 | 386.2 |
| Peptide 18 | 8.9 | 1826 | 205.2 |
| Peptide 19 | 13.7 | 842 | 61.5 |
| Peptide 20 | 31 | 2790 | 90 |
| Peptide 21 | 26.7 | 1134 | 42.4 |
| Peptide 22 | 269 | * | ** |

* The $EC_{50}$ at pH 8 could not be quantified but was greater than 1 mM.
** The Ratio of $EC_{50}$ pH 8/$EC_{50}$ pH 5 could not be calculated because the $EC_{50}$ at pH 8 could not be quantified.

Example 2

Competitive Radioligand-Binding on T84 Cells

Intact human T84 cells from the American Type Culture Collection (ATCC; Manassas, Va.) were used for competitive radioligand-binding experiments. The T84 cells were grown in monolayers on T-150 plastic flasks to 60-70% confluency in Dulbecco's Modified Eagle Medium: Ham's F-12 50/50 media (DMEM/F12)+5% fetal bovine serum (FBS). The cells were harvested by gentle scraping with a cell scraper and cells collected by centrifugation at 2000 g for 10 minutes at 4° C. The cells were washed twice by resuspending gently in phosphate buffered saline (PBS) and collecting them by centrifugation as above.

[$^{125}$I]-STp radioligand was prepared by dissolving 100 μg of NTFYCCELCCNPACAGCY (SEQ ID NO: 71) (Enterotoxin STp; Bachem H-6248) in 0.5 mL water, which was sent to Perkin-Elmer Life and Analytical Sciences (N. Billerica, Mass.) for iodination using the lactoperoxidase method recited in Marchanolis, J. J., "An enzymic method for the trace iodination of immunoglobulins and other proteins", *Biochem. J.* (1969) 113, 299-305. Perkin-Elmer purified the labeled tracer by HPLC using a Waters C-18 μBondapak column (25 cm) previously equilibrated with 10 mM ammonium acetate pH 5.8. A gradient from 0 to 25% acetonitrile was applied to the column in 60 min, followed by isocratic elution at 25% acetonitrile for another 20 min. This method separated two monoiodinated forms from each other and from unlabeled precursor. The second monoiodinated peak (Peak 2), which eluted after 64 min and corresponded to iodination of the fourth tyrosine, was used as the labeled tracer in the assay. The labeled tracer had a specific activity of 2200 Ci/mmol. Upon arrival from Perkin-Elmer, the tracer was stored in aliquots at −20° C.

The binding reactions were assembled in duplicate in 0.2 mL containing: $2.5\times10^5$ T84 cells (0.25 mg protein), 200,000 cpm [$^{125}$I]-STp (41 fmol, 200 pM), 0.1 to 3,000 nM competitor, and 0.5% bovine serum albumin (BSA). The binding assays at pH 5.0 were conducted in DMEM/20 mM 2-(N-morpholino) ethanesulfonic acid (MES). The binding assays at pH 8.0 were performed in DMEM/20 mM N-2-Hydroxyethylpiperazine-N'-2-Ethane Sulfonic Acid (HEPES)/50 mM sodium bicarbonate. The control reactions did not contain a competitor (total) or no cells.

The buffer solutions were prepared first, and then protease-free BSA was added to 0.5%. The radioligand was added to a final concentration of 0.001 μCi/μL. Preparation of competitor peptide stock solutions were made by dissolving peptides to 1 mg/mL in 50 mM sodium phosphate pH 6.0. Concentrations were calculated from the peptide molecular weight provided in the Certificate of Analysis. Competitor dilutions were made in 50 mM sodium phosphate pH 6.0 that contained 20 times the final concentration of peptide to be tested in the binding reaction (20× competitor).

The binding reactions were assembled in the following order:
 i. Radioligand and BSA in buffer solution.
 ii. 10 μL of 20× competitor.
 iii. T84 cells.

The binding reactions were mixed gently and incubated at 37° C. for 1 hr. Separation of membrane bound from free radioligand was conducted by applying the binding reactions to 2.5 cm Whatman GF/C glass-fiber filters (pretreated with 1% polyvinylpyrrolidone in PBS) using vacuum filtration. The filters were rinsed twice with 5 mL ice-cold PBS buffer and measurements of the trapped radioligand were conducted in a scintillation counter. The determination of specific binding was made by subtracting the bound radioactivity from a reaction that contained excess competitor (1 μM) from the bound radioactivity of each sample. The generation of competitive radioligand-binding curves were made using GraphPad Prism (GraphPad Software, San Diego, Calif.), and the data was analyzed with nonlinear regression to calculate the concentration of competitor that resulted in 50% radioligand bound ($IC_{50}$). The apparent dissociation equilibrium constant ($K_i$) for each competitor was obtained from the $IC_{50}$ values and a previously determined estimate of the dissociation constant for the radioligand, $K_d \cong 15$ nM, obtained using the method of Cheng and Prusoff (1973) *Biochem. Pharmacol.* 22(23): 3099-3108. The radioligand concentration of 200 μM used in the assays was very small compared to its dissociation constant, such that the calculated $IC_{50}$ and the $K_i$ values (Table 3) were in effect identical.

TABLE 3

Binding affinity comparisons

| | Binding affinity for GC-C | | |
|---|---|---|---|
| | $K_i$ (nM) | | Ratio $K_i$ pH 8/ |
| Peptide | pH 5 | pH 8 | $K_i$ pH 5 |
| Peptide 1 | 2.9 | 2.0 | 0.69 |
| Peptide 2 | 5.9 | 5.7 | 0.97 |
| Peptide 3 | 14.8 | 259 | 17.5 |
| Peptide 4 | 13.5 | 71.2 | 5.27 |
| Peptide 5 | 29.3 | 162 | 5.52 |
| Peptide 6 | 10.7 | 70.5 | 6.59 |
| Peptide 9 | 20.9 | 26.9 | 1.29 |
| Peptide 10 | 12.4 | 48 | 3.87 |
| Peptide 11 | 2.24 | 14.4 | 6.43 |
| Peptide 12 | 2.30 | 6.2 | 2.70 |
| Peptide 14 | 4.4 | 2.3 | 0.52 |
| Peptide 17 | 4.30 | 27.3 | 6.35 |
| Peptide 20 | 8.5 | 30.6 | 3.6 |
| Peptide 21 | 7.7 | 39.4 | 5.1 |

Example 3

Gastrointestinal Transit in Mice

The purpose of this assay was to test the effect of the guanylate cyclase C peptides on in vivo gastrointestinal transit in mice. Orally-dosed guanylate cyclase C agonists have been demonstrated to increase the % Distance Travelled by a charcoal meal in mice. The assay may be an indicator of the activity of the described guanylate cyclase C peptides to increase upper GI transit in the small intestine of patients.

For the assay, female CD-1 mice (n=10 per group) weighing 25-30 g were fasted overnight and given access to water ad libitum. Activated charcoal (20 g; 100 mesh; Sigma cat #242276) was suspended in a 200 mL gum arabic (100 mg/mL) and stirred for at least one hour. Test peptides were prepared in a 20 mM Tris pH 6.9 vehicle.

Test peptide and vehicle were administered in 200 μL doses by oral gavage. Seven minutes after dosing the test peptides, 200 μL of the charcoal/gum arabic suspension was dosed by oral gavage. After 15 minutes, mice were sacrificed by $CO_2$ overdose. The gastrointestinal tract was removed from the esophagus to the caecum. The total length of the small intestine was measured from the pyloric junction to the ileocaecal junction. The distance travelled by the charcoal was measured from the pyloric junction to the charcoal front. The Distance Travelled (%) was determined as (distance travelled by charcoal/total length of the small intestine)×100. Data were entered into the GraphPad Prism software program and analyzed by ANOVA using a Bonferroni multiple comparison test post-hoc. Plots of data and $ED_{50}$s were also determined using the GraphPad Prism software package.

The dose-dependent effects of acute doses of exemplary peptides on GI transit were determined in female CD mice. The distance traveled by the charcoal front after seven minutes, expressed as a percent of total length of small intestine was used to calculate $ED_{50}$ values (Table 4).

TABLE 4

Potency of exemplary peptides in the gastrointestinal transit assay in mice.

| Peptide | $ED_{50}$ µg/kg |
|---|---|
| Peptide 1 | 0.43 |
| Peptide 2 | 2.06 |
| Peptide 4 | 6.3 |
| Peptide 5 | 7.54 |
| Peptide 10 | 13.7 |
| Peptide 14 | 3.04 |
| Peptide 17 | 2.9 |

Example 4

Effect on cGMP Levels and Secretion in Ligated Intestinal Loops in Rodents

The effect of GC-C agonist peptides on secretion were studied by injecting GC-C agonist peptides described herein directly into an isolated loop in wild-type rats. This was done by surgically ligating three loops in the small intestine in each rat. The methodology for ligated loop formation was similar to that described in London et al. (1997) *Am J Physiol*, p. G93-105. The loops were roughly centered and at lengths of 1-3 cm. The loops were injected with 200 µL of either peptide/GC-C agonist (0.1-5 µg) or vehicle (20 mM Tris, pH 7.5 or Krebs Ringer, 10 mM Glucose, HEPES buffer (KRGH)). Following a recovery time of up to 90 minutes the loops were excised. Weights were recorded for each loop before and after removal of the fluid contained therein. The length of each loop was also recorded. A weight to length ratio (W/L) for each loop was calculated to determine the effects of the GC-C agonist peptide described herein on secretion. Loop fluid volume was also determined. Data, which show an increase in fluid and bicarbonate secretion from ligated duodenal loops in rats after injection of 2.5 µg of peptide per loop, are presented in Table 5.

TABLE 5

Fluid and duodenal bicarbonate secretion in rat intestinal loops

| Peptide | Rate of fluid accumulation µL/min/cm | Rate of $HCO_3^-$ accumulation neq/min/cm |
|---|---|---|
| Vehicle | 0.5 | 10 |
| Peptide 1 | 2.0 | 80 |
| Peptide 2 | 2.0 | 80 |
| Peptide 4 | 2.0 | 80 |
| Peptide 17 | 1.8 | NA |

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A peptide or a pharmaceutically acceptable salt thereof, wherein the peptide comprises the amino acid sequence
Xaa$_1$ Xaa$_2$ Xaa$_3$ Xaa$_4$ Cys$_5$ Xaa$_6$ Xaa$_7$ Xaa$_8$ Cys$_9$ Asn$_{10}$ Pro$_{11}$ Ala$_{12}$ Cys$_{13}$ Xaa$_{14}$ Gly$_{15}$ Xaa$_{16}$ Xaa$_{17}$, (SEQ ID NO:1) or a pharmaceutically acceptable salt thereof; wherein Xaa$_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, α-aminosuberic acid (Asu), α-aminoadipic acid (Aad), or α-aminopimelic acid (Apm);

Xaa$_2$ is Asp, β-carboxylated Asp, Glu, γ-carboxylated Glu, Asu, Aad, Apm, or is absent;

Xaa$_3$ is Asp, β-carboxylated Asp, Glu, γ-carboxylated Glu, Asu, Aad, Apm, or is absent;

Xaa$_4$ is Cys or D-Cys;

Xaa$_6$ is Asp or Glu;

Xaa$_7$ is Tyr, Leu, Phe or Ile;

Xaa$_8$ is Cys or D-Cys;

Xaa$_{14}$ is Thr, Ala or Phe;

Xaa$_{16}$ is Cys or D-Cys; and

Xaa$_{17}$ is Tyr, D-Tyr, or is absent;

wherein:

Xaa$_1$ may be modified on its amino group by methyl, ethanedioic acid, propanedioic acid, butanedioic acid, pentanedioic acid, hexanedioic acid, heptanedioic acid or octanedioic acid; and if both Xaa$_2$ and Xaa$_3$ are absent, then Xaa$_1$ must be β-carboxylated Asp or γ-carboxylated Glu, or Xaa$_1$ must be Asp, D-Asp, Glu, D-Glu, Asu, Aad, Apm and must be modified on its amino group by ethanedioic acid, propanedioic acid, or butanedioic acid, pentanedioic acid, hexanedioic acid, heptanedioic acid or octanedioic acid.

2. The peptide or pharmaceutically acceptable salt thereof according to claim 1, wherein: Xaa$_2$ is Asp or Glu;
Xaa$_2$ and Xaa$_3$ are both present;
Xaa$_3$ is Asp or Glu;
Xaa$_2$ is present and Xaa$_3$ is absent; or
Xaa$_2$ and Xaa$_3$ are both absent.

3. The peptide or pharmaceutically acceptable salt thereof according to claim 1, wherein either or both of Xaa$_2$ and Xaa$_3$ are present and Xaa$_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, Asu, Aad or Apm.

4. The peptide or pharmaceutically acceptable salt thereof according to claim 1, wherein:
Xaa$_6$ is Glu;
Xaa$_7$ is Tyr or Leu;
Xaa$_4$ is Cys;
Xaa$_8$ is Cys;
Xaa$_{14}$ is Thr;
Xaa$_{16}$ is Cys; and
Xaa$_{17}$ is Tyr or absent.

5. The peptide or pharmaceutically acceptable salt thereof according to claim 1, wherein said peptide comprises the amino acid sequence Xaa$_1$ Xaa$_2$ Xaa$_3$ Cys$_4$ Cys$_5$ Glu$_6$ Xaa$_7$ Cys$_8$ Cys$_9$ Asn$_{10}$ Pro$_{10}$ Ala$_{12}$ Cys$_{13}$ Thr$_{14}$ Gly$_{15}$ Cys$_{16}$ Xaa$_{17}$ (SEQ ID NO:2); wherein Xaa$_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;

Xaa$_2$ is Asp or Glu;

Xaa$_3$ is Asp, Glu, or is absent;

Xaa$_7$ is Tyr or Leu; and

Xaa$_{17}$ is Tyr or is absent.

6. The peptide or pharmaceutically acceptable salt thereof according to claim 1, wherein said peptide comprises the amino acid sequence Xaa$_1$ Asp$_2$ Xaa$_3$ Cys$_4$ Cys$_5$ Glu$_6$ Xaa$_7$ Cys$_8$ Cys$_9$ Asn$_{10}$ Pro$_{11}$ Ala$_{12}$ Cys$_{13}$ Thr$_{14}$ Gly$_{15}$ Cys$_{16}$ Xaa$_{17}$ (SEQ ID NO:68); wherein Xaa$_1$ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;

Xaa$_3$ is Asp or is absent;

Xaa$_7$ is Tyr or Leu; and

Xaa$_{17}$ is Tyr or is absent.

7. The peptide or pharmaceutically acceptable salt thereof according to claim 1, wherein said peptide comprises:

Asp Asp Cys Cys Glu Leu Cys Cys Asn Pro Ala Cys Thr Gly Cys (SEQ ID NO:3);

Asp Asp Cys Cys Glu Tyr Cys Cys Asn Pro Ala Cys Thr Gly Cys (SEQ ID NO:4);

Asp Asp Cys Cys Glu Leu Cys Cys Asn Pro Ala Cys Thr Gly Cys Tyr (SEQ ID NO:5);

Asp Asp Cys Cys Glu Tyr Cys Cys Asn Pro Ala Cys Thr Gly Cys Tyr (SEQ ID NO:6);

Asn Asp Asp Cys Cys Glu Leu Cys Cys Asn Pro Ala Cys Thr Gly Cys (SEQ ID NO:7);

Asn Asp Asp Cys Cys Glu Tyr Cys Cys Asn Pro Ala Cys Thr Gly Cys (SEQ ID NO:8);

Asn Asp Asp Cys Cys Glu Leu Cys Cys Asn Pro Ala Cys Thr Gly Cys Tyr (SEQ ID NO:9);

Asn Asp Asp Cys Cys Glu Tyr Cys Cys Asn Pro Ala Cys Thr Gly Cys Tyr (SEQ ID NO:10);

Ala Asp Asp Cys Cys Glu Leu Cys Cys Asn Pro Ala Cys Thr Gly Cys (SEQ ID NO:11);

Ala Asp Asp Cys Cys Glu Tyr Cys Cys Asn Pro Ala Cys Thr Gly Cys (SEQ ID NO:12);

β-Ala Asp Asp Cys Cys Glu Leu Cys Cys Asn Pro Ala Cys Thr Gly Cys (SEQ ID NO:13);

β-Ala Asp Asp Cys Cys Glu Tyr Cys Cys Asn Pro Ala Cys Thr Gly Cys (SEQ ID NO:14);

Ala Asp Asp Cys Cys Glu Leu Cys Cys Asn Pro Ala Cys Thr Gly Cys Tyr (SEQ ID NO:15);

Ala Asp Asp Cys Cys Glu Tyr Cys Cys Asn Pro Ala Cys Thr Gly Cys Tyr (SEQ ID NO:16);

β-Ala Asp Asp Cys Cys Glu Leu Cys Cys Asn Pro Ala Cys Thr Gly Cys Tyr (SEQ ID NO:17);

β-Ala Asp Asp Cys Cys Glu Tyr Cys Cys Asn Pro Ala Cys Thr Gly Cys Tyr (SEQ ID NO:18);

Pro Asp Asp Cys Cys Glu Leu Cys Cys Asn Pro Ala Cys Thr Gly Cys (SEQ ID NO:19);

Pro Asp Asp Cys Cys Glu Tyr Cys Cys Asn Pro Ala Cys Thr Gly Cys (SEQ ID NO:20);

Pro Asp Asp Cys Cys Glu Leu Cys Cys Asn Pro Ala Cys Thr Gly Cys Tyr (SEQ ID NO:21);

Pro Asp Asp Cys Cys Glu Tyr Cys Cys Asn Pro Ala Cys Thr Gly Cys Tyr (SEQ ID NO:22);

Thr Asp Asp Cys Cys Glu Leu Cys Cys Asn Pro Ala Cys Thr Gly Cys (SEQ ID NO:23);

Thr Asp Asp Cys Cys Glu Tyr Cys Cys Asn Pro Ala Cys Thr Gly Cys (SEQ ID NO:24);

Thr Asp Asp Cys Cys Glu Leu Cys Cys Asn Pro Ala Cys Thr Gly Cys Tyr (SEQ ID NO:25);

Thr Asp Asp Cys Cys Glu Tyr Cys Cys Asn Pro Ala Cys Thr Gly Cys Tyr (SEQ ID NO:26);

Gly Asp Asp Cys Cys Glu Leu Cys Cys Asn Pro Ala Cys Thr Gly Cys (SEQ ID NO:27);

Gly Asp Asp Cys Cys Glu Tyr Cys Cys Asn Pro Ala Cys Thr Gly Cys (SEQ ID NO:28);

Gly Asp Asp Cys Cys Glu Leu Cys Cys Asn Pro Ala Cys Thr Gly Cys Tyr (SEQ ID NO:29);

Gly Asp Asp Cys Cys Glu Tyr Cys Cys Asn Pro Ala Cys Thr Gly Cys Tyr (SEQ ID NO:30);
Asp Asp Asp Cys Cys Glu Leu Cys Cys Asn Pro Ala Cys Thr Gly Cys (SEQ ID NO:31);
Asp Asp Asp Cys Cys Glu Tyr Cys Cys Asn Pro Ala Cys Thr Gly Cys (SEQ ID NO:32);
Asp Asp Asp Cys Cys Glu Leu Cys Cys Asn Pro Ala Cys Thr Gly Cys Tyr (SEQ ID NO:33);
Asp Asp Asp Cys Cys Glu Tyr Cys Cys Asn Pro Ala Cys Thr Gly Cys Tyr (SEQ ID NO:34);
Glu Glu Cys Cys Glu Leu Cys Cys Asn Pro Ala Cys Thr Gly Cys (SEQ ID NO:35);
Glu Glu Cys Cys Glu Tyr Cys Cys Asn Pro Ala Cys Thr Gly Cys (SEQ ID NO:36);
Glu Glu Cys Cys Glu Leu Cys Cys Asn Pro Ala Cys Thr Gly Cys Tyr (SEQ ID NO:37);
Glu Glu Cys Cys Glu Tyr Cys Cys Asn Pro Ala Cys Thr Gly Cys Tyr (SEQ ID NO:38);
Glu Glu Glu Cys Cys Glu Leu Cys Cys Asn Pro Ala Cys Thr Gly Cys (SEQ ID NO:39);
Glu Glu Glu Cys Cys Glu Tyr Cys Cys Asn Pro Ala Cys Thr Gly Cys (SEQ ID NO:40);
Glu Glu Glu Cys Cys Glu Leu Cys Cys Asn Pro Ala Cys Thr Gly Cys Tyr (SEQ ID NO:41);
Glu Glu Glu Cys Cys Glu Tyr Cys Cys Asn Pro Ala Cys Thr Gly Cys Tyr (SEQ ID NO:42);
Glu Asp Cys Cys Glu Leu Cys Cys Asn Pro Ala Cys Thr Gly Cys (SEQ ID NO:43);
Glu Asp Cys Cys Glu Tyr Cys Cys Asn Pro Ala Cys Thr Gly Cys (SEQ ID NO:44);
Glu Asp Cys Cys Glu Leu Cys Cys Asn Pro Ala Cys Thr Gly Cys Tyr (SEQ ID NO:45); or
Glu Asp Cys Cys Glu Tyr Cys Cys Asn Pro Ala Cys Thr Gly Cys Tyr (SEQ ID NO:46);
wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

8. The peptide or pharmaceutically acceptable salt thereof according to claim 7, wherein said peptide comprises:
D-Asp Asp Asp Cys Cys Glu Tyr Cys Cys Asn Pro Ala Cys Thr Gly Cys Tyr (SEQ ID NO:47);
D-Ala Asp Asp Cys Cys Glu Tyr Cys Cys Asn Pro Ala Cys Thr Gly Cys Tyr (SEQ ID NO:48);
D-Asn Asp Asp Cys Cys Glu Leu Cys Cys Asn Pro Ala Cys Thr Gly Cys Tyr (SEQ ID NO:49);
D-Ala Asp Asp Cys Cys Glu Leu Cys Cys Asn Pro Ala Cys Thr Gly Cys Tyr (SEQ ID NO:50);
Asp Asp Asp Cys Cys Glu Leu Cys Cys Asn Pro Ala Cys Thr Gly Cys D-Tyr (SEQ ID NO:51);
D-Asp Asp Asp Cys Cys Glu Leu Cys Cys Asn Pro Ala Cys Thr Gly Cys (SEQ ID NO:52);
Asn Asp Asp Cys Cys Glu Tyr Cys Cys Asn Pro Ala Cys Thr Gly Cys Tyr (SEQ ID NO:53);
Asp Asp Cys Cys Glu Tyr Cys Cys Asn Pro Ala Cys Thr Gly Cys Tyr (SEQ ID NO:54);
Asp Asp Asp Cys Cys Glu Tyr Cys Cys Asn Pro Ala Cys Thr Gly Cys Tyr (SEQ ID NO:55);
Gly Asp Asp Cys Cys Glu Tyr Cys Cys Asn Pro Ala Cys Thr Gly Cys Tyr (SEQ ID NO:56);
Pro Asp Asp Cys Cys Glu Tyr Cys Cys Asn Pro Ala Cys Thr Gly Cys Tyr (SEQ ID NO:57);
Ala Asp Asp Cys Cys Glu Tyr Cys Cys Asn Pro Ala Cys Thr Gly Cys Tyr (SEQ ID NO:58);
Asn Asp Asp Cys Cys Glu Leu Cys Cys Asn Pro Ala Cys Thr Gly Cys Tyr (SEQ ID NO:59);
Ala Asp Asp Cys Cys Glu Leu Cys Cys Asn Pro Ala Cys Thr Gly Cys Tyr (SEQ ID NO:60);
β-Ala Asp Asp Cys Cys Glu Leu Cys Cys Asn Pro Ala Cys Thr Gly Cys Tyr (SEQ ID NO:61);
Asp Asp Cys Cys Glu Leu Cys Cys Asn Pro Ala Cys Thr Gly Cys Tyr (SEQ ID NO:62);
Asp Asp Asp Cys Cys Glu Leu Cys Cys Asn Pro Ala Cys Thr Gly Cys Tyr (SEQ ID NO:63);
Pro Asp Asp Cys Cys Glu Leu Cys Cys Asn Pro Ala Cys Thr Gly Cys Tyr (SEQ ID NO:64);
Gly Asp Asp Cys Cys Glu Leu Cys Cys Asn Pro Ala Cys Thr Gly Cys Tyr (SEQ ID NO:65);
Asp Asp Asp Cys Cys Glu Leu Cys Cys Asn Pro Ala Cys Thr Gly Cys (SEQ ID NO:66); or
Glu Glu Glu Cys Cys Glu Tyr Cys Cys Asn Pro Ala Cys Thr Gly Cys Tyr (SEQ ID NO:67).

9. A peptide or a pharmaceutically acceptable salt thereof, wherein the peptide consists of the amino acid sequence
$Xaa_1$ $Xaa_2$ $Xaa_3$ $Xaa_4$ $Cys_5$ $Xaa_6$ $Xaa_7$ $Xaa_8$ $Cys_9$ $Asn_{10}$ $Pro_{11}$ $Ala_{12}$ $Cys_{13}$ $Xaa_{14}$ $Gly_{15}$ $Xaa_{16}$ $Xaa_{17}$, (SEQ ID NO:1) or a pharmaceutically acceptable salt thereof;
wherein
$Xaa_1$ is Asn, D-Asn, Gln, D-Gln, Pro, D-Pro, Ala, O-Ala, D-Ala, Val, D-Val, Gly, Thr, D-Thr, Asp, D-Asp, β-carboxylated Asp, Glu, D-Glu, γ-carboxylated Glu, α-aminosuberic acid (Asu), α-aminoadipic acid (Aad), or α-aminopimelic acid (Apm);
$Xaa_2$ is Asp, β-carboxylated Asp, Glu, γ-carboxylated Glu, Asu, Aad, Apm, or is absent;
$Xaa_3$ is Asp, β-carboxylated Asp, Glu, γ-carboxylated Glu, Asu, Aad, Apm, or is absent;
$Xaa_4$ is Cys or D-Cys;
$Xaa_6$ is Asp or Glu;
$Xaa_7$ is Tyr, Leu, Phe or Ile;
$Xaa_8$ is Cys or D-Cys;
$Xaa_{14}$ is Thr, Ala or Phe;
$Xaa_{16}$ is Cys or D-Cys; and
$Xaa_{17}$ is Tyr, D-Tyr, or is absent;
wherein:
$Xaa_1$ may be modified on its amino group by methyl, ethanedioic acid, propanedioic acid, butanedioic acid, pentanedioic acid, hexanedioic acid, heptanedioic acid or octanedioic acid; and
if both $Xaa_2$ and $Xaa_3$ are absent, then $Xaa_1$ must be β-carboxylated Asp or γ-carboxylated Glu, or $Xaa_1$ must be Asp, D-Asp, Glu, D-Glu, Asu, Aad, Apm and must be modified on its amino group by ethanedioic acid, propanedioic acid, or butanedioic acid, pentanedioic acid, hexanedioic acid, heptanedioic acid or octanedioic acid.

10. The peptide or pharmaceutically acceptable salt thereof according to claim 9, wherein: $Xaa_2$ is Asp or Glu;
$Xaa_2$ and $Xaa_3$ are both present;
$Xaa_3$ is Asp or Glu;
$Xaa_2$ is present and $Xaa_3$ is absent; or
$Xaa_2$ and $Xaa_3$ are both absent.

11. The peptide or pharmaceutically acceptable salt thereof according to claim 9, wherein either or both of $Xaa_2$ and $Xaa_3$ are present and $Xaa_1$ is Asn, D-Asn, Gln, D-Gln, Pro, D-Pro, Ala, β-Ala, D-Ala, Val, D-Val, Gly, Thr, D-Thr, Asp, D-Asp, β-carboxylated Asp, Glu, D-Glu, γ-carboxylated Glu, Asu, Aad or Apm.

12. The peptide or pharmaceutically acceptable salt thereof according to claim 9, wherein:
$Xaa_6$ is Glu;
$Xaa_7$ is Tyr or Leu;
$Xaa_4$ is Cys;
$Xaa_8$ is Cys;

Xaa₁₄ is Thr;
Xaa₁₆ is Cys; and
Xaa₁₇ is Tyr or absent.

13. The peptide or pharmaceutically acceptable salt thereof according to claim 9, wherein said peptide consists of the amino acid sequence Xaa₁ Xaa₂ Xaa₃ Cys₄ Cys₅ Glu₆ Xaa₇ Cys₈ Cys₉ Asn₁₀ Pro₁₁ Ala₁₂ Cys₁₃ Thr₁₄ Gly₁₅ Cys₁₆ Xaa₁₇ (SEQ ID NO:2); wherein
Xaa₁ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;
Xaa₂ is Asp or Glu;
Xaa₃ is Asp, Glu, or is absent;
Xaa₇ is Tyr or Leu; and
Xaa₁₇ is Tyr or is absent.

14. The peptide or pharmaceutically acceptable salt thereof according to claim 9, wherein said peptide consists of the amino acid sequence Xaa₁ Asp₂ Xaa₃ Cys₄ Cys₅ Glu₆ Xaa₇ Cys₈ Cys₉ Asn₁₀ Pro₁₁ Ala₁₂ Cys₁₃ Thr₁₄ Gly₁₅ Cys₁₆ Xaa₁₇ (SEQ ID NO:68); wherein
Xaa₁ is Asn, D-Asn, Gln, D-Gln, Pro, D-Pro, Ala, β-Ala, D-Ala, Val, D-Val, Gly, Thr, D-Thr, Asp, D-Asp, Glu or D-Glu;
Xaa₃ is Asp or is absent;
Xaa₇ is Tyr or Leu; and
Xaa₁₇ is Tyr or is absent.

15. The peptide or pharmaceutically acceptable salt thereof according to claim 9, wherein said peptide consists of:
Asp Asp Cys Cys Glu Leu Cys Cys Asn Pro Ala Cys Thr Gly Cys (SEQ ID NO:3);
Asp Asp Cys Cys Glu Tyr Cys Cys Asn Pro Ala Cys Thr Gly Cys (SEQ ID NO:4);
Asp Asp Cys Cys Glu Leu Cys Cys Asn Pro Ala Cys Thr Gly Cys Tyr (SEQ ID NO:5);
Asp Asp Cys Cys Glu Tyr Cys Cys Asn Pro Ala Cys Thr Gly Cys Tyr (SEQ ID NO:6);
Asn Asp Asp Cys Cys Glu Leu Cys Cys Asn Pro Ala Cys Thr Gly Cys (SEQ ID NO:7);
Asn Asp Asp Cys Cys Glu Tyr Cys Cys Asn Pro Ala Cys Thr Gly Cys (SEQ ID NO:8);
Asn Asp Asp Cys Cys Glu Leu Cys Cys Asn Pro Ala Cys Thr Gly Cys Tyr (SEQ ID NO:9);
Asn Asp Asp Cys Cys Glu Tyr Cys Cys Asn Pro Ala Cys Thr Gly Cys Tyr (SEQ ID NO:10);
Ala Asp Asp Cys Cys Glu Leu Cys Cys Asn Pro Ala Cys Thr Gly Cys (SEQ ID NO:11);
Ala Asp Asp Cys Cys Glu Tyr Cys Cys Asn Pro Ala Cys Thr Gly Cys (SEQ ID NO:12);
β-Ala Asp Asp Cys Cys Glu Leu Cys Cys Asn Pro Ala Cys Thr Gly Cys (SEQ ID NO:13);
β-Ala Asp Asp Cys Cys Glu Tyr Cys Cys Asn Pro Ala Cys Thr Gly Cys (SEQ ID NO:14);
Ala Asp Asp Cys Cys Glu Leu Cys Cys Asn Pro Ala Cys Thr Gly Cys Tyr (SEQ ID NO:15);
Ala Asp Asp Cys Cys Glu Tyr Cys Cys Asn Pro Ala Cys Thr Gly Cys Tyr (SEQ ID NO:16);
β-Ala Asp Asp Cys Cys Glu Leu Cys Cys Asn Pro Ala Cys Thr Gly Cys Tyr (SEQ ID NO:17);
β-Ala Asp Asp Cys Cys Glu Tyr Cys Cys Asn Pro Ala Cys Thr Gly Cys Tyr (SEQ ID NO:18);
Pro Asp Asp Cys Cys Glu Leu Cys Cys Asn Pro Ala Cys Thr Gly Cys (SEQ ID NO:19);
Pro Asp Asp Cys Cys Glu Tyr Cys Cys Asn Pro Ala Cys Thr Gly Cys (SEQ ID NO:20);
Pro Asp Asp Cys Cys Glu Leu Cys Cys Asn Pro Ala Cys Thr Gly Cys Tyr (SEQ ID NO:21);
Pro Asp Asp Cys Cys Glu Tyr Cys Cys Asn Pro Ala Cys Thr Gly Cys Tyr (SEQ ID NO:22);
Thr Asp Asp Cys Cys Glu Leu Cys Cys Asn Pro Ala Cys Thr Gly Cys (SEQ ID NO:23);
Thr Asp Asp Cys Cys Glu Tyr Cys Cys Asn Pro Ala Cys Thr Gly Cys (SEQ ID NO:24);
Thr Asp Asp Cys Cys Glu Leu Cys Cys Asn Pro Ala Cys Thr Gly Cys Tyr (SEQ ID NO:25);
Thr Asp Asp Cys Cys Glu Tyr Cys Cys Asn Pro Ala Cys Thr Gly Cys Tyr (SEQ ID NO:26);
Gly Asp Asp Cys Cys Glu Leu Cys Cys Asn Pro Ala Cys Thr Gly Cys (SEQ ID NO:27);
Gly Asp Asp Cys Cys Glu Tyr Cys Cys Asn Pro Ala Cys Thr Gly Cys (SEQ ID NO:28);
Gly Asp Asp Cys Cys Glu Leu Cys Cys Asn Pro Ala Cys Thr Gly Cys Tyr (SEQ ID NO:29);
Gly Asp Asp Cys Cys Glu Tyr Cys Cys Asn Pro Ala Cys Thr Gly Cys Tyr (SEQ ID NO:30);
Asp Asp Asp Cys Cys Glu Leu Cys Cys Asn Pro Ala Cys Thr Gly Cys (SEQ ID NO:31);
Asp Asp Asp Cys Cys Glu Tyr Cys Cys Asn Pro Ala Cys Thr Gly Cys (SEQ ID NO:32);
Asp Asp Asp Cys Cys Glu Leu Cys Cys Asn Pro Ala Cys Thr Gly Cys Tyr (SEQ ID NO:33);
Asp Asp Asp Cys Cys Glu Tyr Cys Cys Asn Pro Ala Cys Thr Gly Cys Tyr (SEQ ID NO:34);
Glu Glu Cys Cys Glu Leu Cys Cys Asn Pro Ala Cys Thr Gly Cys (SEQ ID NO:35);
Glu Glu Cys Cys Glu Tyr Cys Cys Asn Pro Ala Cys Thr Gly Cys (SEQ ID NO:36);
Glu Glu Cys Cys Glu Leu Cys Cys Asn Pro Ala Cys Thr Gly Cys Tyr (SEQ ID NO:37);
Glu Glu Cys Cys Glu Tyr Cys Cys Asn Pro Ala Cys Thr Gly Cys Tyr (SEQ ID NO:38);
Glu Glu Glu Cys Cys Glu Leu Cys Cys Asn Pro Ala Cys Thr Gly Cys (SEQ ID NO:39);
Glu Glu Glu Cys Cys Glu Tyr Cys Cys Asn Pro Ala Cys Thr Gly Cys (SEQ ID NO:40);
Glu Glu Glu Cys Cys Glu Leu Cys Cys Asn Pro Ala Cys Thr Gly Cys Tyr (SEQ ID NO:41);
Glu Glu Glu Cys Cys Glu Tyr Cys Cys Asn Pro Ala Cys Thr Gly Cys Tyr (SEQ ID NO:42);
Glu Asp Cys Cys Glu Leu Cys Cys Asn Pro Ala Cys Thr Gly Cys (SEQ ID NO:43);
Glu Asp Cys Cys Glu Tyr Cys Cys Asn Pro Ala Cys Thr Gly Cys (SEQ ID NO:44);
Glu Asp Cys Cys Glu Leu Cys Cys Asn Pro Ala Cys Thr Gly Cys Tyr (SEQ ID NO:45); or
Glu Asp Cys Cys Glu Tyr Cys Cys Asn Pro Ala Cys Thr Gly Cys Tyr (SEQ ID NO:46);
wherein the C-terminal amino acid residue may be an L-amino acid residue or a D-amino acid residue and if the N-terminal amino acid residue is Asn, Asp, Ala, Pro, Thr or Glu, the N-terminal residue may be an L-amino acid residue or a D-amino acid residue.

16. The peptide or pharmaceutically acceptable salt thereof according to claim 15, wherein said peptide consists of:
D-Asp Asp Asp Cys Cys Glu Tyr Cys Cys Asn Pro Ala Cys Thr Gly Cys Tyr (SEQ ID NO:47);
D-Ala Asp Asp Cys Cys Glu Tyr Cys Cys Asn Pro Ala Cys Thr Gly Cys Tyr (SEQ ID NO:48);
D-Asn Asp Asp Cys Cys Glu Leu Cys Cys Asn Pro Ala Cys Thr Gly Cys Tyr (SEQ ID NO:49);
D-Ala Asp Asp Cys Cys Glu Leu Cys Cys Asn Pro Ala Cys Thr Gly Cys Tyr (SEQ ID NO:50);
Asp Asp Asp Cys Cys Glu Leu Cys Cys Asn Pro Ala Cys Thr Gly Cys D-Tyr (SEQ ID NO:51);

D-Asp Asp Asp Cys Cys Glu Leu Cys Cys Asn Pro Ala Cys Thr Gly Cys (SEQ ID NO:52);

Asn Asp Asp Cys Cys Glu Tyr Cys Cys Asn Pro Ala Cys Thr Gly Cys Tyr (SEQ ID NO:53);

Asp Asp Cys Cys Glu Tyr Cys Cys Asn Pro Ala Cys Thr Gly Cys Tyr (SEQ ID NO:54);

Asp Asp Asp Cys Cys Glu Tyr Cys Cys Asn Pro Ala Cys Thr Gly Cys Tyr (SEQ ID NO:55);

Gly Asp Asp Cys Cys Glu Tyr Cys Cys Asn Pro Ala Cys Thr Gly Cys Tyr (SEQ ID NO:56);

Pro Asp Asp Cys Cys Glu Tyr Cys Cys Asn Pro Ala Cys Thr Gly Cys Tyr (SEQ ID NO:57);

Ala Asp Asp Cys Cys Glu Tyr Cys Cys Asn Pro Ala Cys Thr Gly Cys Tyr (SEQ ID NO:58);

Asn Asp Asp Cys Cys Glu Leu Cys Cys Asn Pro Ala Cys Thr Gly Cys Tyr (SEQ ID NO:59);

Ala Asp Asp Cys Cys Glu Leu Cys Cys Asn Pro Ala Cys Thr Gly Cys Tyr (SEQ ID NO:60);

β-Ala Asp Asp Cys Cys Glu Leu Cys Cys Asn Pro Ala Cys Thr Gly Cys Tyr (SEQ ID NO:61);

Asp Asp Cys Cys Glu Leu Cys Cys Asn Pro Ala Cys Thr Gly Cys Tyr (SEQ ID NO:62);

Asp Asp Asp Cys Cys Glu Leu Cys Cys Asn Pro Ala Cys Thr Gly Cys Tyr (SEQ ID NO:63);

Pro Asp Asp Cys Cys Glu Leu Cys Cys Asn Pro Ala Cys Thr Gly Cys Tyr (SEQ ID NO:64);

Gly Asp Asp Cys Cys Glu Leu Cys Cys Asn Pro Ala Cys Thr Gly Cys Tyr (SEQ ID NO:65);

Asp Asp Asp Cys Cys Glu Leu Cys Cys Asn Pro Ala Cys Thr Gly Cys (SEQ ID NO:66); or

Glu Glu Glu Cys Cys Glu Tyr Cys Cys Asn Pro Ala Cys Thr Gly Cys Tyr (SEQ ID NO:67).

17. The peptide or pharmaceutically acceptable salt thereof according to claim 1, wherein said peptide or pharmaceutically acceptable salt thereof is isolated or purified.

18. A pharmaceutical composition comprising a pharmaceutically acceptable carrier, a peptide according to claim 1 and one or more agents selected from (i) a cation selected from $Mg^{2+}$, $Ca^{2+}$, $Zn^{2+}$, $Mn^{2+}$, $K^+$, $Na^+$ or $Al^{3+}$, or (ii) a sterically hindered primary amine.

19. The pharmaceutical composition according to claim 18, wherein said $Mg^{2+}$, $Ca^{2+}$, $Zn^{2+}$, $Mn^{2+}$, $K^+$, $Na^+$ or $Al^{3+}$ is provided as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate.

20. The pharmaceutical composition according to claim 18, wherein the sterically hindered primary amine is an amino acid selected from naturally-occurring amino acid, a non-naturally occurring amino acid or an amino acid derivative; and wherein the naturally-occurring amino acid is histidine, phenylalanine, alanine, glutamic acid, aspartic acid, glutamine, leucine, methionine, asparagine, tyrosine, threonine, isoleucine, tryptophan or valine or the non-naturally occurring amino acid is 1-aminocyclohexane carboxylic acid, lanthanine or theanine.

21. The pharmaceutical composition according to claim 20, wherein the sterically hindered primary amine has the formula:

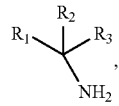

wherein $R_1$, $R_2$ and $R_3$ are independently selected from: H, C(O)OH, $C_1$-$C_6$ alkyl, $C_1$-$C_6$ alkylether, $C_1$-$C_6$ alkylthioether, $C_1$-$C_6$ alkyl carboxylic acid, $C_1$-$C_6$ alkyl carboxylamide and alkylaryl, wherein any group can be singly or multiply substituted with: halogen or amino, and provided that no more than one of $R_1$, $R_2$ and $R_3$ is H.

22. The pharmaceutical composition according to claim 20, wherein the sterically hindered primary amine is selected from cyclohexylamine, 2-methylbutylamine, a polymeric amine, or chitosan.

23. The pharmaceutical composition according to claim 18, further comprising a pharmaceutically acceptable antioxidant, binder, additive, or filler.

24. The pharmaceutical composition according to claim 23, wherein the pharmaceutically acceptable binder or additive is selected from polyvinyl alcohol, polyvinylpyrrolidone (povidone), a starch, maltodextrin or a cellulose ether.

25. The pharmaceutical composition of claim 24, wherein the pharmaceutically acceptable binder or additive is a cellulose ether selected from: methylcellulose, ethylcellulose, carboxymethylcellulose, hydroxyethyl cellulose, hydroxyethyl methylcellulose, hydroxypropyl cellulose and hydroxypropyl methylcellulose.

26. The pharmaceutical composition according to claim 23, wherein the pharmaceutically acceptable filler is cellulose, isomalt, mannitol, lactose or dibasic calcium phosphate.

27. The pharmaceutical composition of claim 26, wherein the pharmaceutically acceptable filler is cellulose selected from microfine cellulose and microcrystalline cellulose.

28. The pharmaceutical composition according to claim 18, further comprising an additional therapeutic agent.

29. The pharmaceutical composition according to claim 28, wherein said additional therapeutic agent is selected from one or more of an analgesic agent, an antidepressant, a pro-motility or prokinetic agent, an antiemetic, an antibiotic, a proton pump inhibitor, an acid blocker, a PDE5 inhibitor, an acid pump antagonist, a GABA-B agonist, a bile acid sequestrant or a mucosal protecting agent.

30. A dosage unit comprising the pharmaceutical composition according to claim 18.

31. The dosage unit according to claim 30, wherein said dosage unit is a capsule, tablet, or comprises 5 μg to 1 mg of said peptide.

32. A method for treating a gastrointestinal disorder comprising administering the pharmaceutical composition according to claim 18.

33. The method according to claim 32, wherein said gastrointestinal disorder is gastroparesis, post-operative gastric ileus, a functional esophageal disorder, a functional gastroduodenal disorder, gastroesophageal reflux disease (GERD), celiac disease, mucositis, or a duodenal or stomach ulcer.

34. The method according to claim 33, wherein said gastrointestinal disorder is gastroparesis selected from idiopathic, diabetic or post-surgical gastroparesis.

35. The method according to claim 33, wherein said gastrointestinal disorder is a functional esophageal disorder selected from functional heartburn, functional chest pain of presumed esophageal origin, functional dysphagia or globus.

36. The method according to claim 33, wherein said gastrointestinal disorder is a functional gastroduodenal disorder selected from functional dyspepsia, a belching disorder, a nausea or vomiting disorder, or rumination syndrome.

* * * * *